United States Patent
Chabrier de Lassauniere et al.

(10) Patent No.: US 6,340,700 B1
(45) Date of Patent: Jan. 22, 2002

(54) 2-(IMINOMETHYL) AMINO-PHENYL DERIVATIVES, PREPARATION, APPLICATION AS MEDICINES AND PHARMACEUTICAL COMPOSITIONS CONTAINING SAME

(75) Inventors: Pierre Etienne Chabrier de Lassauniere, Paris; Serge Auvin, Mauchamps; Dennis Bigg, Gif-sur-Yvette; Michel Auguet, Palaiseau, all of (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 09/381,749

(22) PCT Filed: Feb. 16, 1998

(86) PCT No.: PCT/FR98/00288

§ 371 Date: Sep. 22, 1999

§ 102(e) Date: Sep. 22, 1999

(87) PCT Pub. No.: WO98/42696

PCT Pub. Date: Oct. 1, 1998

(30) Foreign Application Priority Data

Mar. 24, 1997 (FR) .............................. 97 03528

(51) Int. Cl.⁷ ..................... A61K 31/38; A61K 31/35; C07D 333/50; C07D 311/76; C07D 295/00
(52) U.S. Cl. .................. 514/438; 514/447; 514/449; 514/456; 514/637; 549/41; 549/59; 549/356; 549/398; 548/400; 548/469; 544/374; 544/398

(58) Field of Search .................. 514/438, 447, 514/449, 456, 637; 549/41, 59, 356, 398; 548/400, 469

(56) References Cited

U.S. PATENT DOCUMENTS 6,030,985 A * 2/2000 Gentile et al. .............. 514/307

FOREIGN PATENT DOCUMENTS

| WO | 9421621 | 9/1994 |
| WO | 9505363 | 2/1995 |
| WO | 9601817 | 1/1996 |

OTHER PUBLICATIONS

Auvin Serge et al., "BN 80933, a dual inhib. of neuronal NO syn."; Proc. Natl.Acad.Sc.96/19,10824, Feb. 1999.*

* cited by examiner

Primary Examiner—Mukund J. Shah
Assistant Examiner—Sudhaker B. Patel
(74) Attorney, Agent, or Firm—Bierman, Muserlian and Lucas

(57) ABSTRACT

A compound of the formula

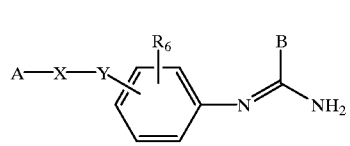

wherein the substituents are defined as in the specification and their pharmaceutically acceptable salts having NOS and ROS activity.

12 Claims, No Drawings

2-(IMINOMETHYL) AMINO-PHENYL DERIVATIVES, PREPARATION, APPLICATION AS MEDICINES AND PHARMACEUTICAL COMPOSITIONS CONTAINING SAME

A subject of the present invention is new derivatives of 2-(iminomethyl)amino-phenyl which have an inhibitory activity on NO-synthase enzymes producing nitrogen monoxide NO and/or an activity which traps the reactive oxygen species (ROS). The invention relates to the derivatives corresponding to general formula (I) defined below, their preparation methods, the pharmaceutical preparations containing them and their use for therapeutic purposes, in particular their use as NO-synthase inhibitors and selective or non selective traps for reactive oxygen species.

Given the potential role of NO and the ROS's in physiopathology, the new derivatives described corresponding to general formula (I) may produce beneficial or favourable effects in the treatment of pathologies where these chemical species are involved. In particular:

- cardiovascular and cerebro-vascular disorders including for example atherosclerosis, migraine, arterial hypertension, septic shock, ischemic or hemorragic cardiac or cerebral infarctions, ischemias and thromboses.
- disorders of the central or peripheral nervous system such as for example neurodegenerative diseases where there can in particular be mentioned cerebral infarctions, sub-arachnoid haemorrhaging, ageing, senile dementias including Alzheimer's disease, Huntington's chorea, Parkinson's disease, Creutzfeld Jacob disease and prion diseases, amyotrophic lateral sclerosis but also pain, cerebral and bone marrow traumas, addiction to opiates, alcohol and addictive substances, erective and reproductive disorders, cognitive disorders, encephalopathies, encephalopathies of viral or toxic origin.
- disorders of the skeletal muscle and neuromuscular joints (myopathy, myosis) as well as cutaneous diseases.
- proliferative and inflammatory diseases such as for example atherosclerosis, pulmonary hypertension, respiratory distress, glomerulonephritis, portal hypertension, psoriasis, arthrosis and rheumatoid arthritis, fibroses, amyloidoses, inflammations of the gastro-intestinal system (colitis, Crohn's disease) or of the pulmonary system and airways (asthma, sinusitis, rhinitis).
- organ transplants.
- auto-immune and viral diseases such as for example lupus, AIDS, parasitic and viral infections, diabetes, multiple sclerosis.
- cancer.
- neurological diseases associated with intoxications (Cadmium poisoning, inhalation of n-hexane, pesticides, herbicides), associated with treatments (radiotherapy) or disorders of genetic origin (Wilson's disease).
- all the pathologies characterized by an excessive production or dysfunction of NO and/or ROS's.

In all these pathologies, there is experimental evidence demonstrating the involvement of NO or ROS's (*J. Med. Chem.* (1995) 38, 4343–4362; *Free Radic. Biol. Med.* (1996) 20, 675–705; *The Neuroscientist* (1997) 3, 327–333).

Furthermore, NO Synthase inhibitors, their use and more recently the combination of these inhibitors with products having antioxidant or antiradicular properties have already been described in previous Patents (respectively U.S. Pat. No. 5,081,148; U.S. Pat. No. 5,360,925 and an unpublished Patent Application).

A subject of the present invention is the derivatives of 2-(iminomethyl)amino-phenyl, their preparation and their therapeutic use.

The compounds of the invention correspond to general formula (I):

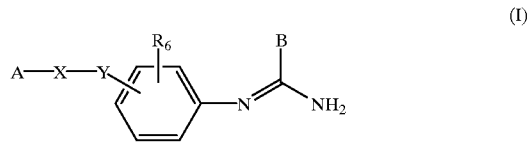

in which:

A represents:
either a

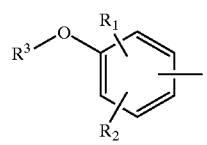

radical in which $R_1$ and $R_2$ represent, independently, a hydrogen atom, a halogen, the OH group, a linear or branched alkyl or alkoxy radical having from 1 to 6 carbon atoms, $R_3$ represents a hydrogen atom, a linear or branched alkyl radical having from 1 to 6 carbon atoms or a —$COR_4$ radical, $R_4$ represents a linear or branched alkyl radical having from 1 to 6 carbon atoms, or a

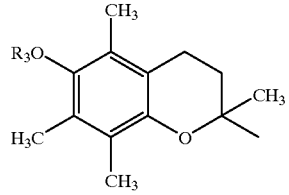

radical in which $R_3$ has the meaning indicated above or a

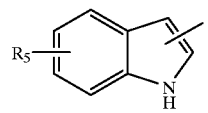

radical in which $R_5$ represents a hydrogen atom, the OH group or a linear or branched alkyl or alkoxy radical having from 1 to 6 carbon atoms;

B represents a linear or branched alkyl radical having from 1 to 6 carbon atoms, carbocyclic or heterocyclic aryl with 5 or 6 members containing from 1 to 4 heteroatoms chosen from O, S, N and in particular the thiophene, furan, pyrrole or thiazole radicals, the aryl radical being optionally substituted by one or more groups chosen from the linear or branched alkyl, alkenyl or alkoxy radicals having from 1 to 6 carbon atoms;

X represents —$Z_1$—, —$Z_1$—CO—, —CH=CH—CO—, —$Z_1$—$NR_3$—CO—, —$Z_1$—$NR_3$—CS—, —$Z_1$—$NR_3$—$SO_2$— or a single bond;

Y represents a radical chosen from the —$Z_2$—Q, piperazine, homopiperazine, 2-methylpiperazine, 2,5-dimethyl-piperazine, 4-aminopiperidine, —$NR_3$—$Z_2$—Q—, —$NR_3$—CO—$Z_2$—Q—, —$NR_3$—NH—CO—$Z_2$—, —NH—NH—$Z_2$—, —$NR_3$—O—$Z_2$—, —$NR_3$—$SO_2$—$NR_3$—$Z_2$—, —O—$Z_2$—Q—, —O—CO—$Z_2$—Q— or —S—$Z_2$—Q— radicals, in which Q represents a single bond, O—$Z_3$, $R_3$—N—$Z_3$ or S—$Z_3$;

$Z_1$, $Z_2$ and $Z_3$ represent independently a single bond or a linear or branched alkylene radical having from 1 to 6 carbon atoms; preferably, $Z_1$, $Z_2$ and $Z_3$ represent —$(CH_2)_m$—, m being an integer comprised between 0 and 6;

$R_6$ represents a hydrogen atom or an OH group;

or are salts of the latter.

The compounds of general formula (I) containing an asymmetrical centre are of isomeric form. The racemic and enantiomeric forms of these compounds also form part of this invention.

The compounds of the invention can exist in the state of bases or of addition salts in particular with organic or inorganic acids or with bases, and in particular in the state of hydrates, hydrochlorides, dihydrochlorides, fumarates or hemifumarates.

By linear or branched alkyl having from 1 to 6 carbon atoms is meant in particular the methyl, ethyl, propyl, isopropyl, butyl, isobutyl, sec-butyl and tert-butyl, pentyl, neopentyl, isopentyl, hexyl, isohexyl radicals. By linear or branched alkoxy having from 1 to 6 carbon atoms is meant radicals the alkyl radical of which has the meaning indicated previously.

By halogen is meant fluorine, chlorine, bromine or iodine atoms.

A particular subject of the invention is the following compounds of general formula (I), described in the examples (in the form of salts in certain cases):

3,5-bis-(1,1-dimethylethyl)-4-hydroxy-N-{4-[(2-thienyl (imino)methyl)amino]phenyl}-benzamide;

3,5-bis-(1,1-dimethylethyl)-4-hydroxy-N-{4-[[(2-thienyl (imino)methyl)amino]phenyl]methyl}-benzamide;

4-acetoxy-3,5-dimethoxy-N-{4-[[(2-thienyl(imino) methyl)amino]phenyl]methyl}-benzamide;

3,5-dimethoxy-4-hydroxy-N-{4-[[(2-thienyl(imino) methyl)amino]phenyl]methyl}-benzamide;

3,5-bis-(1,1-dimethylethyl)-4-hydroxy-N-{4-[2-[(2-thienyl(imino)methyl)amino]phenyl]ethyl}-benzamide;

4-acetoxy-3,5-dimethoxy-N-{4-[2-[(2-thienyl-(imino) methyl)-amino]phenyl]ethyl}-benzamide;

3,5-dimethoxy-4-hydroxy-N-{4-[2-[(2-thienyl-(imino) methyl)-amino]phenyl]ethyl}-benzamide;

3,4,5-trihydroxy-N-{4-[2-[(2-thienyl(imino)methyl)-amino]phenyl]ethyl}-benzamide;

N-{4-[4-[3,5-bis-(1,1-dimethylethyl)-4-hydroxybenzoyl]-1-piperazinyl]-phenyl}-2-thiophenecarboximidamide;

N-{4-[4-[3,5-bis-(1,1-dimethylethyl)-4-hydroxybenzyl]-1-piperazinyl]phenyl}-2-thiophenecarboximdamide;

N-{4-[4-[3,5-dimethoxy-4-hydroxybenzoyl]-1-piperazinyl]-phenyl}-2-thiophenecarboximidamide;

3,4-dihydro-6-hydroxy-2,5,7,8-tetramethyl-N-{4-[(2-thienyl (imino)methyl)amino]phenyl}-2H-1-benzopyran-2-carboxamide;

N-{4-[4-[(3,4-dihydro-6-hydroxy-2,5,7,8-tetramethyl-2H-1-benzopyran-2-yl)carbonyl]-1-piperazinyl] phenyl}-2-thiophenecarboximidamide;

N-{4-[4-[(5-methoxy-1H-indol-3-yl)methylcarbonyl]-1-piperazinyl]phenyl}-2-thiophenecarboximidamide;

N-[4-[4-[{3-[3,5-bis-(1,1-dimethylethyl)-4-hydroxyphenyl]-1-oxo-2-propenyl}-1-piperazinyl]-phenyl]]-2-thiophenecarboximidamide;

3,5-bis-(1,1-dimethylethyl)-4-hydroxy-N-{3-[[(2-thienyl (imino)methyl)amino]phenyl]methyl}-benzamide;

N-[3,5-bis-(1,1-dimethylethyl)-4-hydroxyphenyl]-N'-{{4-[(2-thienyl(imino)methyl)amino]phenyl}methyl}-urea;

N-[5-[{3-(3,5-bis-(1,1-dimethylethyl)-4-hydroxyphenyl)-1-oxo-2-propenyl}amino]-2-hydroxyphenyl]-2-thiophenecarboximidamide;

N-[3-[{3-(3,5-bis-(1,1-dimethylethyl)-4-hydroxyphenyl)-1-oxo-2-propenyl}-amino]-4-hydroxyphenyl]-2-thiophenecarboximidamide;

N-{4-[4-[3,4,5-trihydroxybenzoyl]-1-piperazinyl] phenyl}-2-thiophenecarboximidamide;

N-[3,5-bis-(1,1-dimethylethyl)-4-hydroxyphenyl]-N'-{{4-[(2-thienyl(imino)methyl)amino] phenyl}carbonylamino}-urea;

N-[3,5-bis-(1,1-dimethylethyl)-4-hydroxyphenyl]-N'-{{4-[(2-thienyl(imino)methyl)amino]phenyl}methyl}-thiourea;

N-[3,5-bis-(1,1-dimethylethyl)-4-hydroxyphenyl]-N'-{2-{4-[(2-thienyl(imino)methyl)amino]phenyl}ethyl}-urea;

N-(4-{4-[(3,4-dihydro-6-methoxy-2,5,7,8-tetramethyl-2H-1-benzopyran-2-yl)carbonyl]-1-piperazinyl}phenyl)-2-thiophenecarboximidamide;

N-[4-{4-[(3,4-dihydro-6-hydroxy-2,5,7,8-tetramethyl-2H-1-benzopyran-2-yl)carbonyl]-1H-1,4-diazepin-1-yl}phenyl]-2-thiophenecarboximidamide;

(R)-N-{4-[4-[(3,4-dihydro-6-hydroxy-2,5,7,8-tetramethyl-2H-1-benzopyran-2-yl)carbonyl]-1-piperazinyl]phenyl}-2-thiophenecarboximidamide;

(S)-N-{4-[4-[(3,4-dihydro-6-hydroxy-2,5,7,8-tetramethyl-2H-1-benzopyran-2-yl)carbonyl]-1-piperazinyl]phenyl}-2-thiophenecarboximidamide;

3,5-bis-(1,1-dimethylethyl)-4-hydroxy-N-{2-[3-[(2-thienyl(imino)methyl)amino]phenyl]ethyl}-benzamide;

N-{4-(4-[2-(3,5-bis-(1,1-dimethylethyl)-4-hydroxyphenyl)-1-oxo-ethyl]-1-piperazinyl)phenyl}-2-thiophene-carboximidamide;

2-{4-[(2-thienyl(imino)methyl)amino]phenyl}ethyl 3,5-bis-(1,1-dimethylethyl)-4-hydroxy-benzoate 2-{3-[(2-thienyl(imino)methyl)amino]phenyl}ethyl 3,5-bis-(1,1-dimethylethyl)-4-hydroxy-benzoate 2-{2-[(2-thienyl(imino)methyl)amino]phenyl}ethyl 3,5-bis-(1,1-dimethylethyl)-4-hydroxy-benzoate as well as their salts, in particular their hydrochlorides, dihydrochlorides, fumarates or hemi-fumarates.

There will generally be preferred the compounds of general formula (I) for which:

X represents a linear or branched alkylene radical having from 1 to 6 carbon atoms and Y represents a piperazine, homopiperazine, 2-methylpiperazine, 2,5-dimethylpiperazine, 4-aminopiperidine, —$NR_3$—$Z_2$—Q—, —$NR_3$—NH—CO—$Z_2$—, —NH—NH—$Z_2$— or —$NR_3$—O—$Z_2$— radical;

or

X represents —$Z_1$—CO— or —CH=CH—CO— and Y represents a piperazine, homopiperazine, 2-methylpiperazine, 2,5-dimethylpiperazine, 4-aminopiperidine, —$NR_3$—$Z_2$—Q—, —$NR_3$—NH—CO—$Z_2$—, —NH—NH—$Z_2$—, —$NR_3$—O—$Z_2$—, —O—$Z_2$—Q— radical or —$NR_3$—CO—Q'— radical with Q'=$R_3$—N—$Z_3$;

or

X represents —$Z_1$—$NR_3$—CO— and Y represents —$Z_2$—Q—, —NH—$Z_2$—Q—, —NH—CO—$Z_2$—Q"— with Q"=O—$Z_3$—, $R_3$—N—$Z_3$— or S—$Z_3$—, or Y represents —$NR_3$—$SO_2$—$NR_3$—$Z_2$— or —O—$Z_2$—Q—;

or

X represents —$Z_1$—NH—CO— and Y represents a piperazine, homopiperazine, 2-methylpiperazine, 2,5-dimethylpiperazine, 4-aminopiperidine, —$NR_3$—$Z_2$—Q—, —$NR_3$—NH—CO—$Z_2$—, —NH—NH—$Z_2$— or —$NR_3$—O—$Z_2$— radical;

or

X represents —$Z_1$—$NR_3$—$SO_2$— and Y represents —$Z_2$—Q"— with Q"=O—$Z_3$—, $R_3$—N—$Z_3$— or S—$Z_3$—, or Y represents —$NR_3$—$Z_2$—Q—;

or

X represents —$Z_1$— and Y represents —O—CO—$Z_2$—Q—;

or

X represents —$Z_1$—$NR_3$—CS— and Y represents —NH—$Z_2$—Q—, or a piperazine, homopiperazine, 2-methylpiperazine, 2,5-dimethyl-piperazine, 4-aminopiperidine, —$NR_3$—$Z_2$—Q—, —NH—NH—$Z_2$— or —$NR_3$—O—$Z_2$— radical;

or

X represents a bond and Y represents —O—$Z_2$—NH—, —S—$Z_2$—NH—.

Moreover, the X-Y group will preferably be chosen from the following radicals:

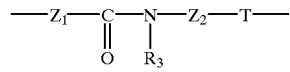

in which T represents a single bond, the —$NR_3$— radical or the —CO—$NR_3$— radical, or

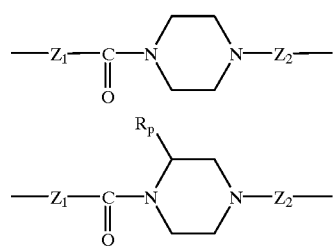

in which $R_p$ represents a hydrogen atom or a methyl radical, or

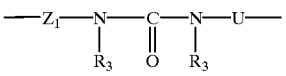

in which U represents a —$Z_2$—, —$NR_3$—CO—, —CO—$Z_2$—O—, —CO—, —$NR_3$— radical or an oxygen atom, or

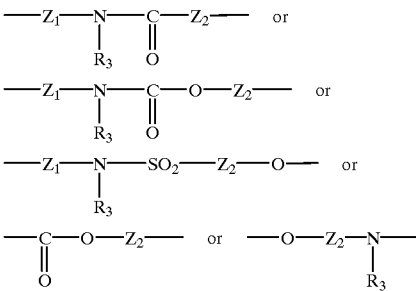

the $Z_1$, $Z_2$ and $R_3$ radicals having the meaning indicated above.

In a preferential manner, the compounds according to the invention will be one of the following compounds:

3,5-bis-(1,1-dimethylethyl)-4-hydroxy-N-{4-[2-[(2-thienyl(imino)methyl)amino]phenyl]ethyl}-benzamide;

3,4,5-trihydroxy-N-{4-[2-[(2-thienyl(imino)methyl)-amino]phenyl]ethyl}-benzamide;

N-{4-[4-[3,5-bis-(1,1-dimethylethyl)-4-hydroxybenzoyl]-1-piperazinyl]phenyl}-2-thiophenecarboximidamide;

N-{4-[4-[3,5-bis-(1,1-dimethylethyl)-4-hydroxybenzyl]-1-piperazinyl]phenyl}-2-thiophenecarboximidamide;

3,4-dihydro-6-hydroxy-2,5,7,8-tetramethyl-N-{4-[(2-thienyl (imino)methyl)amino]phenyl}-2H-1-benzopyran-2-carboxamide;

N-{4-[4-[(3,4-dihydro-6-hydroxy-2,5,7,8-tetramethyl-2H-1-benzopyran-2-yl)carbonyl]-1-piperazinyl]phenyl}-2-thiophenecarboximidamide;

N-{4-[4-[(5 methoxy-1H-indol-3-yl)methylcarbonyl]-1-piperazinyl]phenyl}-2-thiophenecarboximidamide;

3,5-bis-(1,1-dimethylethyl)-4-hydroxy-N-{3-[[(2-thienyl (imino)methyl)amino]phenyl]methyl}-benzamide;

N-[3,5-bis-(1,1-dimethylethyl)-4-hydroxyphenyl]-N'-{{4-[(2-thienyl(imino)methyl)amino]phenyl}methyl}-urea;

N-[5-[{3-(3,5-bis-(1,1-dimethylethyl)-4-hydroxyphenyl)-1-oxo-2-propenyl}-amino]-2-hydroxyphenyl]-2-thiophenecarboximidamide;

N-[3-[{3-(3,5-bis-(1,1-dimethylethyl)-4-hydroxyphenyl)-1-oxo-2-propenyl}-amino]-4-hydroxyphenyl]-2-thiophenecarboximidamide;

N-{4-[4-[3,4,5-trihydroxybenzoyl]-1-piperazinyl]phenyl}-2-thiophenecarboximidamide;

N-[3,5-bis-(1,1-dimethylethyl)-4-hydroxyphenyl]-N'-{{4-[(2-thienyl(imino)methyl)amino]phenyl}carbonylamino}-urea;

or a salt of one of the latter, in particular a hydrochloride, dihydrochloride, fumarate or hemi-fumarate of one of the latter.

Other preferred compounds for the invention will be the following compounds:

4-acetoxy-3,5-dimethoxy-N-{4-[2-[(2-thienyl-(imino)methyl)-amino]phenyl]ethyl}-benzamide;

3,5-dimethoxy-4-hydroxy-N-{4-[2-[(2-thienyl-(imino)methyl)-amino]phenyl]ethyl}-benzamide;
or a salt of one of the latter, in particular a hydrochloride, dihydrochloride, fumarate or hemi-fumarate of one of the latter.

Quite particularly preferred compounds of the invention will be as follows:

N-{4-[4-[(3,4-dihydro-6-hydroxy-2,5,7,8-tetramethyl-2H-1-benzopyran-2-yl)carbonyl]-1-piperazinyl] phenyl}-2-thiophenecarboximidamide;

(R)-N-{4-[4-[(3,4-dihydro-6-hydroxy-2,5,7,8-tetramethyl-2H-1-benzopyran-2-yl)carbonyl]-1-piperazinyl]phenyl}-2-thiophenecarboximidamide;

(S)-N-{4-[4-[(3,4-dihydro-6-hydroxy-2,5,7,8-tetramethyl-2H-1-benzopyran-2-yl)carbonyl]-1-piperazinyl]phenyl}-2-thiophenecarboximidamide;

or a salt of one of the latter, in particular a hydrochloride, dihydrochloride, fumarate or hemi-fumarate of one of the latter.

Finally, there will be particularly preferred for the invention the compounds of general formula (I) presenting the following characteristics:
either:
A represents:

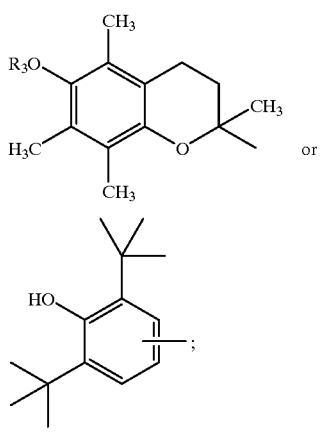

X represents —CO— or —NH—CO—;
and Y represents an —NH—$Z_2$—Q— or piperazine radical, Q representing a single bond or an O—$Z_3$, $R_3$—N—$Z_3$ or S—$Z_3$ radical, and $Z_2$ and $Z_3$ representing independently a bond or a linear or branched alkylene radical having from 1 to 6 carbon atoms and $R_3$ represents a hydrogen atom or a linear or branched alkyl radical having from 1 to 6 carbon atoms.
or: $R_6$ is an OH group.

A subject of the invention is also, as medicaments, the compounds of general formula (I) described previously or their pharmaceutically acceptable salts. It also relates to pharmaceutical compositions containing these compounds or their pharmaceutically acceptable salts, and the use of these compounds or of their pharmaceutically acceptable salts for producing medicaments intended to inhibit neuronal NO synthase or inductible NO synthase, to inhibit lipidic peroxidation or to provide the double function of NO synthase inhibition and lipidic peroxidation.

By pharmaceutically acceptable salt is meant in particular addition salts of inorganic acids such as hydrochloride, sulphate, phosphate, diphosphate, hydrobromide and nitrate, or of organic acids, such as acetate, maleate, fumarate, tartrate, succinate, citrate, lactate, methane sulphonate, p-toluenesulphonate, pamoate, oxalate and stearate. The salts formed from bases such as sodium or potassium hydroxide also fall within the scope of the present invention, when they can be used. For other examples of pharmaceutically acceptable salts, reference can be made to "Pharmaceutical salts", *J. Pharm. Sci.* 66:1 (1977).

The pharmaceutical composition can be in the form of a solid, for example powders, granules, tablets, capsules, liposomes or suppositories. Appropriate solid supports can be for example calcium phosphate, magnesium stearate, talc, sugars, lactose, dextrin, starch, gelatin, methyl cellulose, sodium carboxymethyl cellulose, polyvinylpyrrolidine and wax.

The pharmaceutical compositions containing a compound of the invention can also be presented in the form of a liquid, for example, solutions, emulsions, suspensions or syrups. Appropriate liquid supports can be, for example, water, organic solvents such as glycerol or the glycols, as well as their mixtures, in varying proportions, in water.

A medicament according to the invention can be administered by topical, oral or parenteral route, by intramuscular injection, etc.

The envisaged administration dose for the medicament according to the invention is comprised between 0.1 mg and 10 g according to the type of active compound used.

The invention also offers, as new industrial products, the synthetic intermediates of the products of general formula (I), namely the products of general formula (II)A:

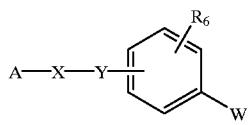

(II)A in which:

W represents an amino or nitro radical,

A represents:

either a

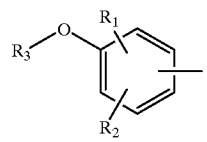

radical in which $R_1$ and $R_2$ represent, independently, a hydrogen atom, a halogen, the OH group, a linear or branched alkyl or alkoxy radical having from 1 to 6 carbon atoms, $R_3$ represents a hydrogen atom, a linear or branched alkyl radical having from 1 to 6 carbon atoms or a —$COR_4$ radical, $R_4$ representing a linear or branched alkyl radical having from 1 to 6 carbon atoms, or a

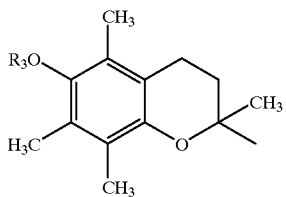

radical in which $R_3$ has the meaning indicated above or a

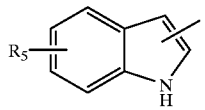

radical in which $R_5$ represents a hydrogen atom, the OH group or a linear or branched alkyl or alkoxy radical having from 1 to 6 carbon atoms;

X represents —$Z_1$—, —$Z_1$—CO—, —CH=CH—CO—, —$Z_1$—$NR_3$—CO—, —$Z_1$—$NR_3$—CS—, —$Z_1$—$NR_3$—$SO_2$— or a single bond;

Y represents a radical chosen from the —$Z_2$—Q, piperazine, homopiperazine, 2-methylpiperazine, 2,5-dimethylpiperazine, 4-aminopiperidine, —$NR_3$—$Z_2$—Q—, —$NR_3$—CO—$Z_2$—Q—, —$NR_3$—NH—CO—$Z_2$—, —NH—NH—$Z_2$—, —$NR_3$—O—$Z_2$—, —$NR_3$—$SO_2$—$NR_3$—$Z_2$—, —O—$Z_2$—Q—, —O—CO—$Z_2$—Q— or —S—$Z_2$—Q— radicals, in which Q represents a single bond, O—$Z_3$, $R_3$—N—$Z_3$ or S—$Z_3$;

$Z_1$, $Z_2$ and $Z_3$ represent independently a single bond or a linear or branched alkylene radical having from 1 to 6 carbon atoms; preferably, $Z_1$, $Z_2$ and $Z_3$ represent —$(CH_2)_m$, m being an integer comprised between 0 and 6;

$R_6$ represents a hydrogen atom or an OH group;

with the exception however of 3,5-bis-(1,1-dimethylethyl)-4-hydroxy-N-(4-nitrophenyl)-benzamide;

or the salts of the latter.

Moreover, the invention offers in particular, as new industrial products, the following compounds, which are synthetic intermediates of products of general formula (I):

3,5-bis-(1,1-dimethylethyl)-4-hydroxy-N-(4-aminophenyl)-benzamide;
3,5-bis-(1,1-dimethylethyl)-4-hydroxy-N-[(4-nitrophenyl)methyl]-benzamide;
3,5-bis-(1,1-dimethylethyl)-4-hydroxy-N-[(4-aminophenyl)methyl]-benzamide;
4-acetoxy-3,5-dimethoxy-N-[(4-nitrophenyl)methyl]-benzamide;
4-acetoxy-3,5-dimethoxy-N-[(4-aminophenyl)methyl]-benzamide;
3,5-bis-(1,1-dimethylethyl)-4-hydroxy-N-[2-(4-nitrophenyl)ethyl]-benzamide;
3,5-bis-(1,1-dimethylethyl)-4-hydroxy-N-[2-(4-aminophenyl)ethyl]-benzamide;
4-acetoxy-3,5-dimethoxy-N-[2-(4-nitrophenyl)ethyl]-benzamide;
4-acetoxy-3,5-dimethoxy-N-[2-(4-aminophenyl)ethyl]-benzamide;
3,4,5-trihydroxy-N-[2-(4-nitrophenyl)ethyl]-benzamide;
3,4,5-trihydroxy-N-[2-(4-aminophenyl)ethyl]-benzamide;
2,6-bis-(1,1-dimethylethyl)-4-{[4-(4-nitrophenyl)-1-piperazinyl]-carbonyl}-phenol;
2,6-bis-(1,1-dimethylethyl)-4-{[4-(4-aminophenyl)-1-piperazinyl]-carbonyl}-phenol;
2,6-bis-(1,1-dimethylethyl)-4-{[4-(4-nitrophenyl)-1-piperazinyl]-methyl}-phenol;
2,6-bis-(1,1-dimethylethyl)-4-{[4-(4-aminophenyl)-1-piperazinyl]-methyl}-phenol;
2,6-dimethoxy-4-{[4-(4-nitrophenyl)-1-piperazinyl]carbonyl}-phenol;
2,6-dimethoxy-4-{[4-(4-aminophenyl)-1-piperazinyl]carbonyl}-phenol;
3,4-dihydro-6-hydroxy-2,5,7,8-tetramethyl-N-(4-nitrophenyl)-2H-1-benzopyran-2-carboxamide;
3,4-dihydro-6-hydroxy-2,5,7,8-tetramethyl-N-(4-aminophenyl)-2H-1-benzopyran-2-carboxamide;
3,4-dihydro-2,5,7,8-tetramethyl-2-{4-[(4-nitrophenyl)-1-piperazinyl]-carbonyl}-2H-1-benzopyran-6-ol;
3,4-dihydro-2,5,7,8-tetramethyl-2-{4-[(4-aminophenyl)-1-piperazinyl]-carbonyl}-2H-1-benzopyran-6-ol;
1-[(5 methoxy-1H-indol-3-yl)methylcarbonyl]-4-(4-nitrophenyl)-piperazine;
1-[(5 methoxy-1H-indol-3-yl)methylcarbonyl]-4-(4-aminophenyl)-piperazine;
2,6-bis-(1,1-dimethylethyl)-4-{3-[4-(4-nitrophenyl)-1-piperazinyl]-3-oxo-2-propenyl}-phenol;
2,6-bis-(1,1-dimethylethyl)-4-{3-[4-(4-aminophenyl)-1-piperazinyl]-3-oxo-2-propenyl}-phenol;
3,5-bis-(1,1-dimethylethyl)-4-hydroxy-N-[(3-nitrophenyl)methyl]-benzamide;
3,5-bis-(1,1-dimethylethyl)-4-hydroxy-N-[(3-aminophenyl)methyl]-benzamide;
N-[3,5-bis-(1,1-dimethylethyl)-4-hydroxyphenyl]-N'-[(4-nitrophenyl)methyl]-urea;
N-[(4-aminophenyl)methyl]-N'-[3,5-bis-(1,1-dimethylethyl)-4-hydroxyphenyl]-urea;
3-[(3,5-bis-(1,1-dimethylethyl)-4-hydroxyphenyl]-N-(4-hydroxy-3-nitrophenyl)-2-propenamide;
3-[(3,5-bis-(1,1-dimethylethyl)-4-hydroxyphenyl]-N-(4-hydroxy-3-aminophenyl)-2-propenamide;
3-[(3,5-bis-(1,1-dimethylethyl)-4-hydroxyphenyl]-N-(2-hydroxy-5-nitrophenyl)-2-propenamide;
3-[(3,5-bis-(1,1-dimethylethyl)-4-hydroxyphenyl]-N-(2-hydroxy-5-aminophenyl)-2-propenamide;
5-{[4-(4-nitrophenyl)-1-piperazinyl]carbonyl}-benzene-1,2,3-triol;
5-{[4-(4-aminophenyl)-1-piperazinyl]carbonyl}-benzene-1,2,3-triol;
N-[3,5-bis-(1,1-dimethylethyl)-4-hydroxyphenyl]-N'-[(4-nitrophenyl)-carbonylamino]-urea;
N-[(4-aminophenyl)carbonylamino]-N'-[3,5-bis-(1,1-dimethylethyl)-4-hydroxyphenyl]-urea;
N-[3,5-bis-(1,1-dimethylethyl)-4-hydroxyphenyl]-N'-[(4-nitrophenyl)methyl]-thiourea;
N-[(4-aminophenyl)methyl]-N'-[3,5-bis-(1,1-dimethylethyl)-4-hydroxyphenyl]-thiourea;

N-[3,5-bis-(1,1-dimethylethyl)-4-hydroxyphenyl]-N'-[2-(4-nitrophenyl)ethyl]-urea;

N-[2-(4-aminophenyl)ethyl]-N'-[3,5-bis-(1,1-dimethylethyl)-4-hydroxyphenyl]-urea;

1-{[3,4-dihydro-6-methoxy-2,5,7,8-tetramethyl-2H-1-benzopyran-2-yl]carbonyl}-4-(4-nitrophenyl)piperazine;

1-{[3,4-dihydro-6-methoxy-2,5,7,8-tetramethyl-2H-1-benzopyran-2-yl]carbonyl}-4-(4-aminophenyl)piperazine;

hexahydro-4-(4-nitrophenyl)-1H-1,4-diazepine;

1-[(3,4-dihydro-6-hydroxy-2,5,7,8-tetramethyl-2H-1-benzopyran-2-yl)carbonyl]hexahydro-4-(4-nitrophenyl)-1H-1,4-diazepine;

1-(4-aminophenyl)-4-[(3,4-dihydro-6-hydroxy-2,5,7,8-tetramethyl-2H-1-benzopyran-2-yl)carbonyl]hexahydro-1H-1,4-diazepine;

hydrochloride du N-[4-{4-[(3,4-dihydro-6-hydroxy-2,5,7,8-tetramethyl-2H-1-benzopyran-2-yl)carbonyl]-1H-1,4-diazepin-1-yl}phenyl]-2-thiophenecarboximidamide hydrochloride;

(R)-3,4-dihydro-2,5,7,8-tetramethyl-2-{4-[(4-nitrophenyl)-1-piperazinyl]-carbonyl}-2H-1-benzopyran-6-ol;

(R)-3,4-dihydro-2,5,7,8-tetramethyl-2-{4-[(4-aminophenyl)-1-piperazinyl]-carbonyl}-2H-1-benzopyran-6-ol;

(S)-3,4-dihydro-2,5,7,8-tetramethyl-2-{4-[(4-nitrophenyl)-1-piperazinyl]-carbonyl}-2H-1-benzopyran-6-ol;

(S)-3,4-dihydro-2,5,7,8-tetramethyl-2-{4-[(4-aminophenyl)-1-piperazinyl]-carbonyl}-2H-1-benzopyran-6-ol;

3,5-bis-(1,1-dimethylethyl)-4-hydroxy-N-[2-(3-nitrophenyl)ethyl]-benzamide;

3,5-bis-(1,1-dimethylethyl)-4-hydroxy-N-[2-(3-aminophenyl)ethyl]-benzamide;

2-(4-nitrophenyl)ethyl 3,5-bis-(1,1-dimethylethyl)-4-hydroxybenzoate;

2-(4-aminophenyl)ethyl 3,5-bis-(1,1-dimethylethyl)-4-hydroxy-benzoate;

or their salts.

Finally, the invention offers processes for the preparation of compounds of general formula (I) as defined above and consisting, for example, of the reaction in a lower alcohol such as methanol, ethanol, isopropyl alcohol or t-butanol, preferably in isopropyl alcohol, at a temperature comprised between 20 and 90° C., for example at 50° C., and for 1 to 48 hours, preferably for 15 to 24 hours, optionally in the presence of DMF, of a compound of general formula (III) as defined above with a compound of general formula (IV)

(IV)

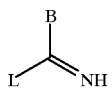

said compound of general formula (IV) being optionally salified by a mineral acid G, B having the meaning indicated above and L representing a leaving group and in particular an alkoxy, thioalkyl, sulphonic acid, halide, aryl alcohol or tosyl radical (other leaving groups well known to a person skilled in the art which can optionally be used for the invention are described in the following work: *Advanced Organic Chemistry*, J. March, 3rd Edition (1985), Mc Graw-Hill, p. 315). Preferably, G represents HCl, HBr or HI.

Other production processes can be envisaged and can be consulted in the literature (for example: The Chemistry of amidines and imidates, Vol. 2, Saul PATAI and Zvi RAPPOPORT, John Wiley & Sons, 1991).

According to the invention, the compounds of general formula (I) can be prepared by the process described below.

Preparation of Compounds of General Formula (I):

The compounds of general formula (I) can be prepared from intermediates of general formula (II) according to diagram 1.

The reduction of the nitro function of the intermediates of general formula (II) is generally carried out by catalytic hydrogenation in ethanol, in the presence of Pd/C, except when X=—CH=CH—CO— or Y=—O—CH$_2$—, the nitro group is selectively reduced using, for example, SnCl$_2$ (*J. Heterocyclic Chem.* (1987), 24, 927–930; *Tetrahedron Letters* (1984), 25, (8), 839–842). The reaction is then carried out by heating the mixture to approx. 70° C., for at least three hours, in ethyl acetate, sometimes with added ethanol.

The aniline derivatives of general formula (III) thus obtained can be condensed on derivatives of general formula (IV), for example derivatives of O-alkyl thioimidate or S-alkyl thioimidate type, in order to produce final compounds of general formula (I) (cf. diagram 1). For example, for B=thiophene, the derivatives of general formula (III) can be condensed on S-methylthiophene thiocarboxamide hydriodide, prepared according to a method in the literature (*Ann. Chim.* (1962), 7, 303–337). Condensation can be carried out by heating in an alcohol (for example in methanol or isopropanol), optionally in the presence of DMF at a temperature comprised between 50 and 100° C. for a duration generally comprised between a few hours and overnight.

Diagram 1:

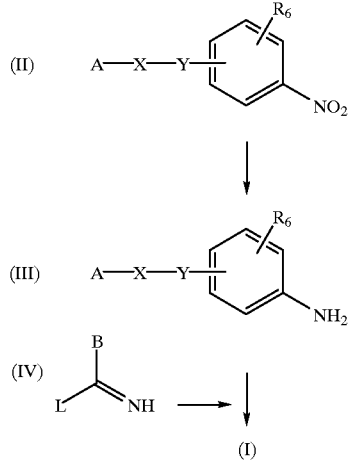

Preparation of Intermediates of General Formula (II):

The intermediates of general formula (II) can be prepared by different processes depending on the chemical functions which are set up: amines, carboxamides, ureas, thioureas, sulphonamides, aminosulphonylureas, sulphamides, carbamates, ethers, esters, thioethers, acylureas, etc.:

When:

X=linear or branched alkylene radical having from 1 to 6 carbon atoms and Y=piperazine, homopiperazine, 2-methylpiperazine, 2,5-dimethylpiperazine, 4-aminopiperidine, —NR$_3$—Z$_2$—Q—, —NR$_3$—NH—CO—Z$_2$—, —NH—NH—Z$_2$—, —NR$_3$—O—Z$_2$—

The amines of general formula (II), diagram 2, in which A, X, Y and $R_6$ are as defined above, can be obtained by nucleophile substitution of the halogenated derivatives of general formula (VI) by an amine of general formula (VII). The reaction is carried out, for example, in DMF in the presence of $K_2CO_3$ at 20° C. The halogenated derivatives of general formula (VI) can be accessed, for example, by bromation of the primary alcohols of general formula (V) using $PBr_3$, at 0° C., in anhydrous THF. The alcohols of general formula (V) which are not commercially available can be prepared according to methods described in the literature (*Tetrahedron Lett.* (1983), 24, (24), 2495–2496).

Diagram 2:

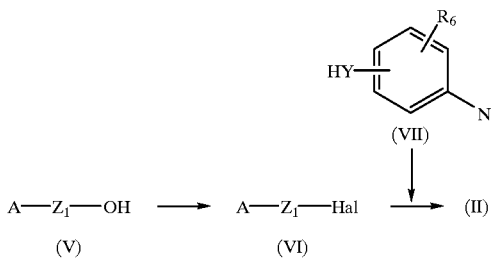

The amines of general formula (VII) in which Y represents homopiperazine, 2,5-dimethylpiperazine, 4-aminopiperidine or more generally —$NR_3$—$Z_2$—$NR_3$— are synthesized in three stages from the corresponding commercial diamines. The diamines are selectively mono-protected in the form of the carbamate (*Synthesis* (1984), (12), 1032–1033; *Synth. Commun.* (1990), 20, (16), 2559–2564) before reaction by nucleophile substitution on a fluoronitrobenzene, in particular 4-fluoronitrobenzene. The amines, previously protected, are released at the last stage, according to methods described in the literature (T. W. Greene and P. G. M. Wuts, Protective Groups in Organic Synthesis, Second Edition (Wiley-Interscience, 1991)), in order to produce intermediates of general formula (VII). When:

X=—$Z_1$—CO—, —CH=CH—CO— and Y=piperazine, homopiperazine, 2-methylpiperazine, 2,5-dimethylpiperazine, 4-aminopiperidine, —$NR_3$—$Z_2$—Q—, —$NR_3$—NH—CO—$Z_2$—, —NH—NH—$Z_2$—, —$NR_3$—O—$Z_2$—

The carboxamides of general formula (II), diagram 3, in which A, X, Y and $R_6$ are as defined above, are prepared by condensation of the commercial carboxylic acids of general formula (VIII) for X=—$Z_1$CO— and of general formula (IX) for X=—CH=CH—CO— with amines of general formula (VII). The non commercial acids can be synthesized according to methods similar to those described in the literature (*J. Org. Chem.* (1974), 39 (2), 219–222; *J. Amer. Chem. Soc.* (1957), 79, 5019–5023, and *CHIMIA* (1991), 45 (4), 121–123 when A represents a 6-alkoxy-2,5,7,8-tetramethylchromane radical). The amines of general formula (VII) in which Y represents homopiperazine, 2,5-dimethylpiperazine, 4-aminopiperidine, or more generally —$NR_3$—$Z_2$—$NR_3$— are prepared according to methods similar to those described in the previous paragraph. The carboxamide bonds are formed under standard conditions for peptide synthesis (M. Bodanszky and A. Bodanszky, The Practice of Peptide Synthesis, 145 (Springer-Verlag, 1984)) in THF, dichloromethane or DMF in the presence of a coupling reagent such as dicyclohexylcarbodiimide (DCC), 1.1'-carbonyldiimidazole (CDI) (*J. Med. Chem.* (1992), 35 (23), 4464–4472) or 1-(3-dimethylaminopropyl)-3-ethylcarbodiimide hydrochloride (EDC or WSCI) (John Jones, The chemical synthesis of peptides, 54 (Clarendon Press, Oxford, 1991)).

Diagram 3:

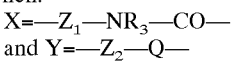

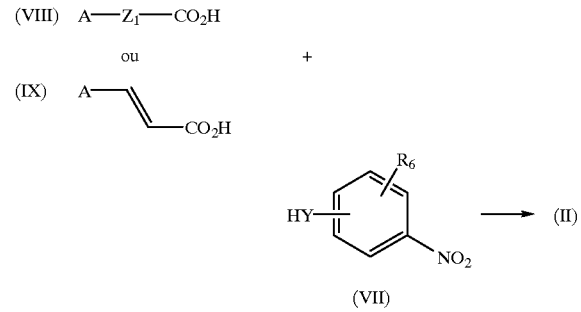

When:
X=—$Z_1$—$NR_3$—CO—
and Y=—$Z_2$—Q—

The carboxamides of general formula (II) in which A, X, Y and $R_6$ are as defined above can also be prepared, as in diagram 4, by peptide condensation of an amine of general formula (X) with a commercial acid of general formula (XI). When X=—$NR_3$—CO— and $R_3$=H, the compounds of general formula (X) are anilines which are obtained by hydrogenation, in the presence of a catalytic quantity of Pd/C, the corresponding nitrobenzene derivatives, themselves synthesized according to a method described in the literature (*J. Org. Chem.* (1968), 33 (1), 223–226). When X—$NR_3$—CO— and $R_3$ is a linear or branched alkyl radical having from 1 to 6 carbon atoms, the monoalkylamines can be obtained according to a process described in the literature (U.S. Pat. Nos. 3,208,859 and 2,962,531). The non-commercial carboxylic acids of general formula (XI) can be accessed using methods described in the literature (*Acta Chem. Scand.* (1983), 37, 911–916; *Synth. Commun.* (1986), 16 (4), 479–483; *Phophorus, Sulphur Silicon Relat. Elem.* (1991), 62, 269–273).

Diagram 4:

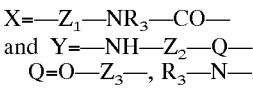

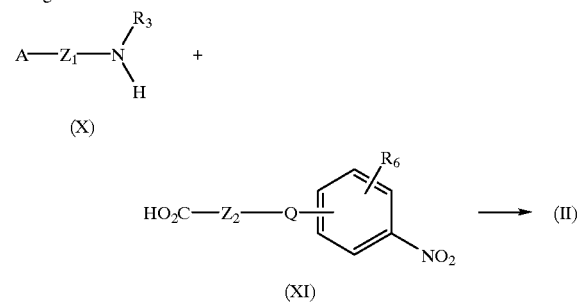

When:
X=—$Z_1$—$NR_3$—CO—
and Y=—NH—$Z_2$—Q—, —NH—CO—$Z_2$—Q— with Q=O—$Z_3$—, $R_3$—N—$Z_3$— or S—$Z_3$—, The ureas of general formula (II), diagram 5, in which A, X, Y and $R_6$ are as defined above, are prepared by the addition of an amine of general formula (X) on an isocyanate of general formula (XII), (XIII) or (XIV) in a solvent such as chloroform at 20° C. Synthesis of non-commercial isocyanates of general formula (XII) is described in the literature (*J. Med. Chem.* (1992), 35 (21), 3745–3754). The halogenated intermediate ureas (XV) and (XVII) are then substituted by a derivative of general formula (XVI), in which Q represents O—$Z_3$—, $R_3$—N—$Z_3$— or S—$Z_3$—, in the presence of a base such as, for example, $K_2CO_3$ or NaH in an aprotic solvent such as THF or DMF in order to finally obtain ureas of general formula (II).

Diagram 5:

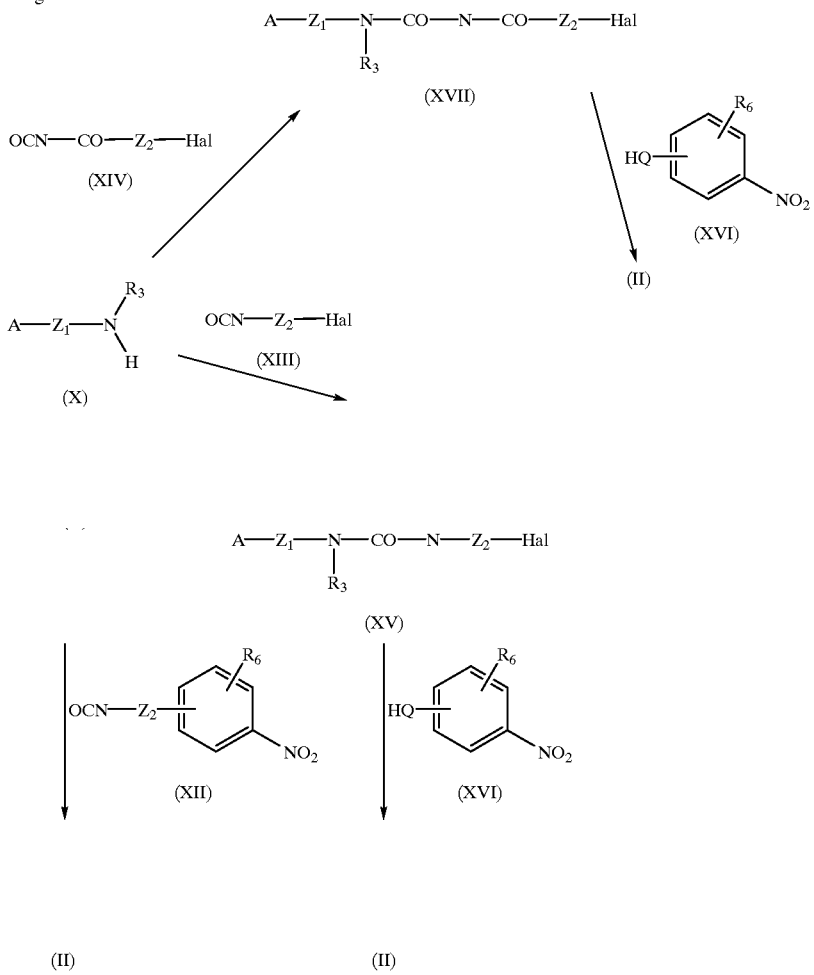

When:

X=—$Z_1$—NH—CO— and Y=piperazine, homopiperazine, 2-methylpiperazine, 2,5-dimethylpiperazine, 4-aminopiperidine, —$NR_3$—$Z_2$—Q—, —$NR_3$—NH—CO—$Z_2$—, —NH—NH—$Z_2$—, —$NR_3$—O—$Z_2$—

The ureas of general formula (II), diagram 6, in which A, X, Y and $R_6$ are as defined above, are prepared by the addition of an amine of general formula (VII), described previously, onto an isocyanate of general formula (XVIII) in the presence of a base such as diisopropylethylamine.

The isocyanates of general formula (XVIII) are synthesized from primary amines of general formula (X), described previously, triphosgene and a tertiary amine (*J. Org. Chem.* (1994), 59 (7), 1937–1938).

The amines of general formula (VII) in which Y—NH—O— are prepared according to a method described in the literature (*J. Org. Chem.* (1984), 49 (8), 1348–1352).

Diagram 6:

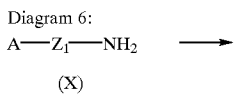

-continued

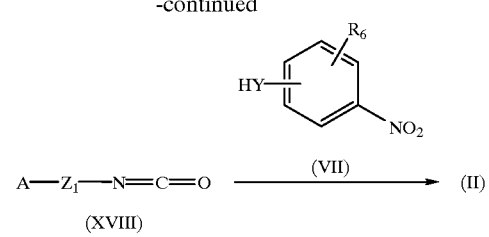

When:

X=—$Z_1$—$NR_3$—CO— and Y=—$NR_3$—$SO_2$—$NR_3$—$Z_2$—

The aminosulphonylureas of general formula (II), diagram 7, in which A, X, Y and $R_6$ are as defined above, are prepared by the addition of amines of general formula (X), described previously, onto chlorosulphonylisocyanate (*J. Med. Chem.* (1996), 39 (6), 1243–1252). The intermediate chlorosulphonylurea (XIX) is then condensed on the amines of general formula (VII), described previously, in order to produce the aminosulphonylureas of general formula (II) which can optionally be alkylated by a halogenated derivative in the presence of a base such as, for example, NaH in order to produce derivatives of general formula (II).

Diagram 7:

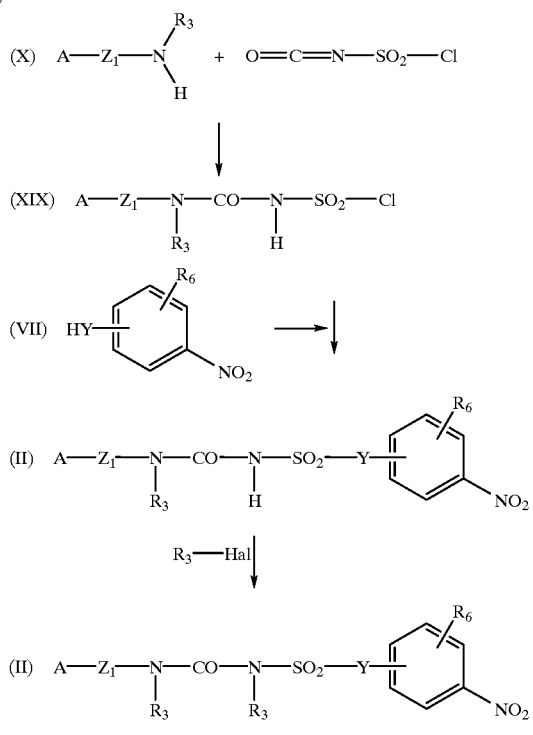

When:
X=—$Z_1$—$NR_3$—$SO_2$—
and Y=—$Z_2$—Q—, with Q=O—$Z_3$—, $R_3$—N—$Z_3$— or S—$Z_3$—, The sulphonamides of general formula (II), diagram 8, in which A, X, Y and $R_6$ are as defined above, are prepared by the addition of amines of general formula (X), described previously, onto halogenoalkylsulphonyl chlorides of general formula (XX). The halogenoalkylsulphonamides of general formula (XXI), obtained intermediately, are then condensed on an alcohol, an amine or a thiol of general formula (XVI) in the presence of a base such as, for example, $K_2CO_3$ or NaH, in a polar solvent such as, for example, acetonitrile or DMF.

Diagram 8:

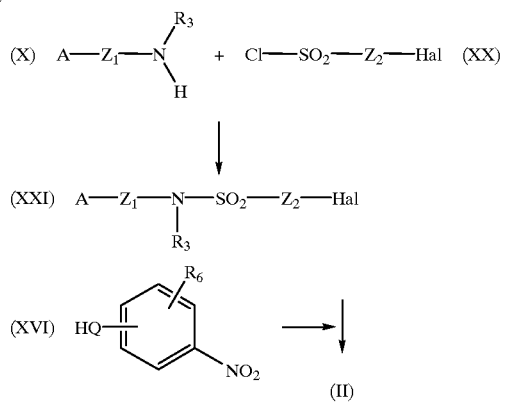

When:
X=—$Z_1$—$NR_3$—$SO_2$—
and Y=—$NR_3$—$Z_2$—Q—

The sulphamides of general formula (II), diagram 9, in which A, X, Y and $R_6$ are as defined above are prepared in three stages from amines of general formula (X) and chlorosulphonylisocyanate. The reaction of an alcohol, such as tBuOH, on the isocyanate function of chlorosulphonylisocyanate (*Tetrahedron Lett.* (1991), 32 (45), 6545–6546) leads to an intermediate of chlorosulphonylcarbamate type, which reacts in the presence of an amine of general formula (X) to produce a derivative of carboxylsulphamide type of general formula (XXII). The treatment of this intermediate in a strong acid medium produces the sulphamide derivative of general formula (XXIII). Alkylation of the compounds of general formula (XXIII) by the halogenated derivatives of general formula (XXIV) in the presence of a base such as, for example, NaH in a polar aprotic solvent allows sulphamide derivatives of general formula (II) to be obtained.

Diagram 9:

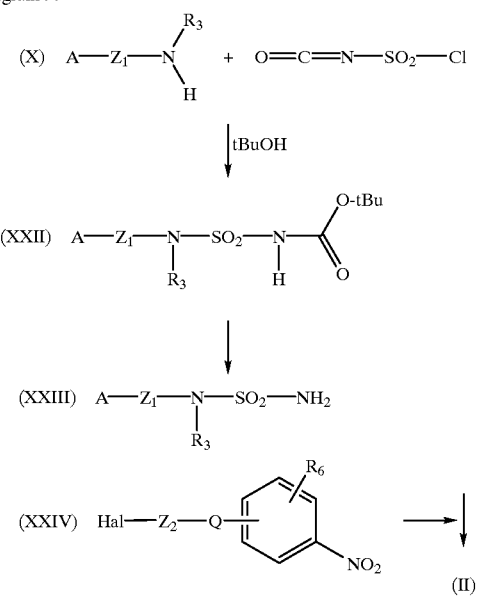

When:
X=—$Z_1$—$NR_3$—CO— and Y=—O—$Z_2$—Q—

The carbamates of general formula (II), diagram 10, in which A, X, Y and $R_6$ are as defined above, are prepared by the reaction of amines of general formula (X), described previously, with chloroformate derivatives of general formula (XXV) prepared according to a method described in the literature (*Tetrahedron Lett.* (1993), 34 (44), 7129–7132).

Diagram 10:

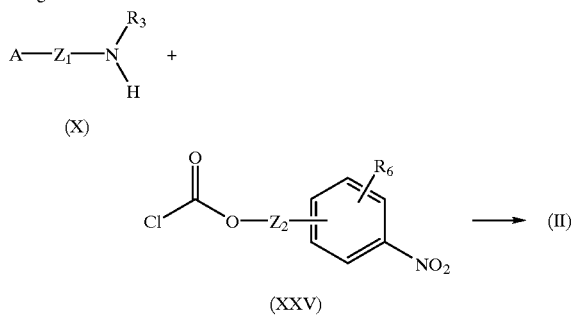

When: X=—$Z_1$—CO—, —CH=CH—CO—
and Y=—O—$Z_2$—Q—

The esters of general formula (II), diagram 11, in which A, X, Y and $R_6$ are as defined above, are prepared by the reaction of acids of general formula (VIII) or (IX) and alcohols of general formula (XXVI) in the presence de dicyclohexylcarbodiimide and of a catalytic quantity of 4-dimethylaminopyridine in a solvent such as, for example, THF or DMF at 20° C.

Diagram 11:

(VIII) A—$Z_1$—$CO_2H$ ou +

(IX) 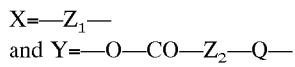

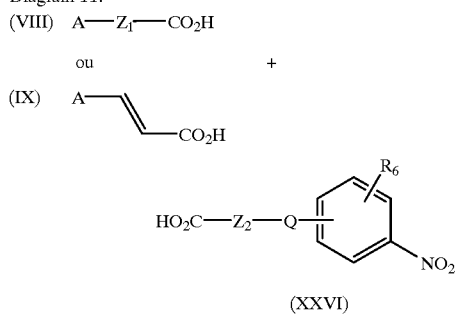 → (II)

(XXVI)

When:
X=—$Z_1$—
and Y=—O—CO—$Z_2$—Q—

The esters of general formula (II), diagram 12, in which A, X, Y and $R_6$ are as defined above, can also be prepared by the reaction of acids of general formula (XI), described previously, with the alcohols of general formula (V) under the conditions described previously.

Diagram 12:
(VIII) A—$Z_1$—OH +

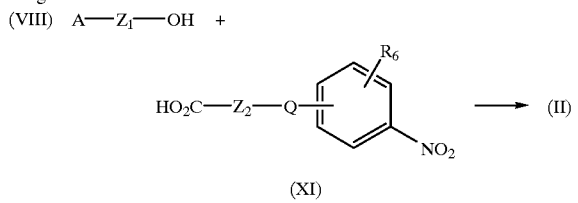 → (II)

(XI)

When:
X=—$Z_1$—$NR_3$—CS—
and Y=—NH—$Z_2$—Q—, piperazine, homopiperazine, 2-methylpiperazine, 2,5-dimethylpiperazine, 4-aminopiperidine, —$NR_3$—$Z_2$—Q—, —NH—NH—$Z_2$—, —$NR_3$—O—$Z_2$—

The thioureas of general formula (II) in which A, X, Y and $R_6$ are as defined above, are prepared from the ureas described previously using Lawesson's reagent, following an experimental protocol described in the literature (*J. Med. Chem.* (1995), 38 (18), 3558–3565).

When:
X represents a bond
Y=—O—$Z_2$—Q—, —S—$Z_2$—Q—
and Q=—HN—

The etheroxides or thioetheroxides of general formula (II), diagram 13, in which A, X, Y and $R_6$ are as defined above are prepared from dihydroquinones of general formula (XXVII) (*J. Chem. Soc.*, Perkin Trans. I, (1981), 303–306) or thiophenols of general formula (XXVIII) (*Bio. Med. Chem. Letters*, (1993), 3 (12), 2827–2830) and an electrophile ($E^+$) such as, for example, bromoacetonitrile or 4-nitrophenyloxazolinone, in the presence of $K_2CO_3$ (*J. Heterocyclic Chem.*, (1994), 31, 1439–1443). The nitrites must be reduced (lithium hydride or catalytic hydrogenation) in order to produce intermediates of general formula (XXIX) or (XXX). The opening of the nitrophenyloxazolinones, accessible by reaction of the corresponding nitroanilines with chloroethylchloroformate as described in the literature (*J. Am. Chem. Soc.*, (1953), 75, 4596), by phenols or thiophenols leads directly to compounds of general formula (XXIX) or (XXX) which are then condensed on fluoronitrobenzene in order to produce intermediates of general formula (II).

Diagram 13:

(XXVII) A—OH    A—SH    (XXVIII)

$E^+$ ↓       $E^+$ ↓

(XXIX) AO—$Z_2$—$NH_2$    AS—$Z_2$—$NH_2$    (XXX)

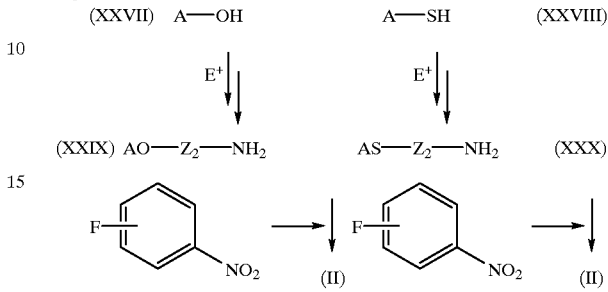

When:
X represents —$Z_1$—CO— or —CH=CH—CO—
Y=—$NR_3$—CO—Q—
and Q=$R_3$—N—$Z_3$

The acylureas of general formula (II), diagram 14, in which A, X, Y and $R_6$ are as defined above are prepared by condensation of acids of general formula (VIII) or (IX), diagram 3, and ureas of general formula (XXXI) in the presence of a coupling agent usually used in peptide synthesis, as described previously, in a solvent such as, for example, dichloromethane or DMF. The ureas of general formula (XXXI) are accessible from isocyanates of general formula (XII), diagram 5, according to a method in the literature (*J. Chem. Soc.*, Perkin Trans. 1, (1985), (1), 75–79).

Diagram 14:
(VIII) A—$Z_1$—$CO_2H$ ou +

(IX) 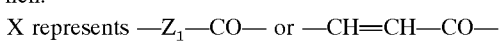

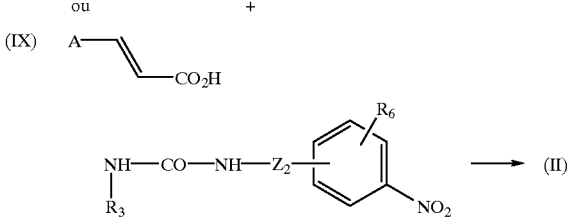 → (II)

Unless they are defined differently, all the technical and scientific terms used here have the same meaning as that usually understood by an ordinary specialist in the field to which the invention belongs. Similarly, all publications, Patent Applications, Patents and other references mentioned here are incorporated by way of reference.

The following examples are presented to illustrate the above procedures and should in no way be considered as restricting the scope of the invention.

EXAMPLES

Example 1

3,5-bis-(1,1-dimethylethyl)-4-hydroxy-N-{4-[(2-thienyl (imino)methyl)amino]phenyl}-benzamide hydrochloride: 1

1.1) 3,5-bis-(1,1-dimethylethyl)-4-hydroxy-N-(4-nitrophenyl)-benzamide:

1.38 g (10 mmoles) of 4-nitroaniline, 2.5 g (10 mmoles) of 3,5-di-tert-butyl-4-hydroxybenzoic acid and 2.26 g (11 mmoles) of dicyclohexylcarbodiimide are introduced into a 250 ml flask containing 20 ml of THF. The reaction medium is agitated for 15 hours at ambient temperature, and the precipitate which appears is filtered out and rinsed with ethyl acetate. After the solution is concentrated under reduced pressure, the residue is diluted in 20 ml of ethyl acetate and the insoluble part is filtered out. The solvent is eliminated under vacuum and the residue is precipitated from diethyl ether. The solid is recovered by filtration, rinsed abundantly with diethyl ether in order to produce a white powder with a yield of 65%. Melting point: 277–278° C.

NMR $^1$H (100 MHz, DMSO d6, δ): 10.72 (s, 1H, CONH); 8.30 (m, 4H, Ph-NO$_2$); 7.80 (s, 2H, Ph); 1.60 (s, 18H, 2× tBu).

1.2) 3,5-bis-(1,1-dimethylethyl)-4-hydroxy-N-(4-aminophenyl)-benzamide:

In a 250 ml Parr flask, 2.4 g (6.5 mmoles) of 3,5-bis-(1,1-dimethylethyl)-4-hydroxy-N-(4-nitrophenyl)-benzamide is dissolved in 50 ml of an absolute ethanol/dichloromethane mixture (1/1) in the presence of 10% Pd/C. The mixture is agitated under 20 PSI of hydrogen, at 30° C., for one hour. After filtration on celite, the filtrate is concentrated under vacuum. The evaporation residue is taken up in 25 ml of a 1M HCl solution. The precipitate formed is filtered and rinsed with 50 ml of diethyl ether followed by 50 ml of ethyl acetate. The amine is released from its salt by agitation in a mixture of 50 ml of ethyl acetate and 50 ml of 1M NaOH. After decanting, the organic phase is washed with 25 ml of 1M NaOH and 25 ml of brine. The organic solution is dried over sodium sulphate, filtered, rinsed and concentrated to dryness under reduced pressure to produce 1.09 g (49%) of a white powder. Melting point: 220–221° C.

NMR $^1$H (100 MHz, DMSO d6, δ): 9.80 (s, 1H, CONH); 7.78 (s, 2H, Ph); 7.05 (m, 4H, Ph-NH$_2$); 5.02 (s, 2H, OH); 1.60 (s, 18H, 2× tBu).

1.3) 3,5-bis-(1,1-dimethylethyl)-4-hydroxy-N-{4-[(2-thienyl (imino)methyl)-amino]phenyl}-benzamide hydrochloride: 1

880 mg (3.08 mmoles) of S-methyl-2-thiophenethiocarboximide hydriodide (Ann. Chim. (1962), 7, 303–337) is introduced into a 100 ml flask containing a solution of 1.05 g (3.08 mmoles) of 3,5-bis-(1,1-dimethylethyl)-4-hydroxy-N-(4-aminophenyl)-benzamide in 20 ml of 2-propanol. After heating at 50° C. for 15 hours, the reaction medium is concentrated to dryness under vacuum. The residue is taken up in 50 ml of ethyl acetate and 50 ml of a saturated solution of sodium carbonate. After decanting, the organic phase is washed successively with 50 ml of a saturated solution of sodium carbonate, 50 ml of water and 50 ml of brine. The organic solution is dried over sodium sulphate, filtered and evaporated under reduced pressure. The crystals obtained are taken up in diethyl ether, filtered and washed successively with ethyl acetate and acetone. 0.77 g of base is obtained with a yield of 58%.

The hydrochloride is prepared from 0.77 g (1.71 mmole) of base dissolved in 60 ml of methanol and salified in the presence of 3.42 ml (3.42 mmoles) of a molar solution of HCl in anhydrous diethyl ether. After agitating for 30 minutes at ambient temperature, the solvent is evaporated off under vacuum and the residue precipitated in the presence of diethyl ether. The crystals obtained are filtered and rinsed abundantly with diethyl ether in order to finally produce after drying 0.65 g (43%) of a pale yellow powder. Melting point: 290–291° C.

NMR $^1$H (400 MHz, DMSO d6, δ): 11.55 (s, 1H, NH$^+$); 10.40 (s, 1H, CONH); 9.83 (s, 1H, NH$^+$); 8.85 (s, 1H, NH$^+$); 8.21 (m, 2H, thiophene); 7.70 (s, 2H, Ph); 7.67 (m, 4H, Ph-NH); 7.60 (s, 1H, OH); 7.40 (m, 1H, thiophene); 1.42 (s, 18H, 2× tBu). IR: $v_{OH}$: 3624 cm$^{-1}$, 3430 cm$^{-1}$; $v_{C=O}$ (amide): 1653 cm$^{-1}$; $v_{C=N}$ (amidine): 1587 cm$^{-1}$.

Example 2

3,5-bis-(1,1-dimethylethyl)-4-hydroxy-N-{4-[[(2-thienyl-(imino)methyl)amino]phenyl]methyl}-benzamide hydrochloride: 2

2.1) 3,5-bis-(1,1-dimethylethyl)-4-hydroxy-N-[(4-nitrophenyl)methyl]-benzamide:

1.88 g (10 mmoles) of p-nitrobenzylamine hydrochloride, 2.5 g (10 mmoles) of 3,5-di-tert-butyl-4-hydroxybenzoic acid, 1.38 ml (10 mmoles) of triethylaamine and 2.26 g (11 mmoles) of dicyclohexylcarbodiimide are introduced into a 250 ml flask containing 25 ml of THF. The reaction medium is agitated for 15 hours at ambient temperature, the precipitate which appears is filtered out and rinsed with the minimum quantity of ethyl acetate. After concentration of the solution under reduced pressure, the residue is precipitated from a mixture of ethyl acetate/diethyl ether (1/4) and filtered. The crystals are washed abundantly with diethyl ether in order to finally produce, after drying, a white powder with a yield of 74% (2.85 g). Melting point: 230–231° C.

NMR $^1$H (100 MHz, CDCl$_3$, δ): 7.85 (m, 4H, Ph-NO$_2$); 7.69 (s, 2H, Ph); 6.82 (m, 1H, NHCO); 5.67 (s, 1H, OH); 4.75 (d, 2H, CH$_2$—NHCO, J=6.5 Hz); 1.49 (s, 18H, 2× tBu).

2.2) 3,5-bis-(1,1-dimethylethyl)-4-hydroxy-N-[(4-aminophenyl)methyl]-benzamide:

In a 250 ml Parr flask, 2.85 g (7.4 mmoles) of 3,5-bis-(1,1-dimethylethyl)-4-hydroxy-N-[(4-nitrophenyl)methyl]-benzamide is dissolved in 30 ml of an absolute ethanol/dichloromethane mixture (1/1) in the presence of 10% Pd/C. The mixture is agitated under 20 PSI of hydrogen, at 30° C., for one hour. After filtration on celite, the filtrate is concentrated under vacuum. The evaporation residue crystallizes spontaneously. It is left to rest overnight, the crystals are filtered out and rinsed with a mixture of diethyl ether (45 ml) and acetone (5 ml). 1.63 g (62%) of a white powder is obtained. Melting point: 188–189° C.

NMR $^1$H (100 MHz, CDCl$_3$, δ): 7.62 (s, 2H, Ph); 6.95 (m, 4H, Ph-NH$_2$); 6.20 (m, 1H, NHCO); 5.58 (s, 1H, OH); 4.50 (d, 2H, CH$_2$—NHCO, J=6.5 Hz); 3.70 (wide s, 2H, NH$_2$); 1.47 (s, 18H, 2× tBu).

2.3) 3,5-bis-(1,1-dimethylethyl)-4-hydroxy-N-{4-[[(2-thienyl-(imino)methyl)-amino]phenyl]methyl}-benzamide hydrochloride: 2

The experimental protocol used is the same as that described for compound 1, with 3,5-bis-(1,1-dimethylethyl)-4-hydroxy-N-[(4-aminophenyl)methyl]-benzamide replacing the 3,5-bis-(1,1-dimethylethyl)-4-hydroxy-N-(4-aminophenyl)-benzamide. After salification with a molar solution of HCl in anhydrous diethyl ether, a white powder is obtained with a yield of 56%. Melting point: 218–219° C.

NMR $^1$H (400 MHz, DMSO d6, δ): 11.60 (s, 1H, NH$^+$); 9.83 (s, 1H, NH$^+$); 9.02 (s, 1H, CONH); 8.90 (s, 1H, NH$^+$); 8.18 (m, 2H, thiophene); 7.70 (s, 2H, Ph); 7.42 (m, 6H, thiophene, Ph-NH, OH); 4.50 (d, 2H, CH$_2$—NHCO, J=5.7 Hz); 1.40 (s, 18H, 2× tBu). IR: $v_{OH}$: 3624 cm$^{-1}$, 3424 cm$^{-1}$; $v_{C=O}$ (amide): 1644 cm$^{-1}$; $v_{C=N}$ (amidine): 1568 cm$^{-1}$.

Example 3

4-acetoxy-3,5-dimethoxy-N-{4-[[(2-thienyl(imino) methyl)amino]phenyl]methyl}-benzamide: 3

3.1) 4-acetoxy-3,5-dimethoxy-benzoic acid:

In a 100 ml flask, under a nitrogen atmosphere, 1.50 g (7.57 mmoles) of syringic acid is dissolved in 15 ml of dry pyridine. 0.86 ml (9.08 mmoles) of acetic anhydride is added dropwise and the mixture is agitated at ambient temperature for 18 hours. The pyridine is evaporated off under reduced pressure, the residue is taken up in 25 ml of dichloromethane and washed with 10 ml of a molar solution of HCl then with 2×10 ml of water. The organic phase is dried over sodium sulphate, filtered and evaporated under vacuum. 1.72 g (95%) of a beige powder is obtained. Melting point: 181–183° C.

NMR $^1$H (100 MHz, CDCl$_3$, δ): 8.15 (s, 1H, CO$_2$H); 7.40 (s, 2H, Ph); 3.90 (s, 6H, 2× OCH$_3$); 2.40 (s, 3H, CH$_3$).

3.2) 4-acetoxy-3,5-dimethoxy-N-[(4-nitrophenyl)methyl]-benzamide:

The experimental protocol used is the same as that described for intermediate 2.1, 4-acetoxy-3,5-dimethoxy-benzoic acid replacing the 3,5-di-tert-butyl-4-hydroxy-benzoic acid. A colourless oil is obtained with a yield of 28%.

NMR $^1$H (100 MHz, DMSO d6, δ): 9.26 (t, 1H, NHCO, J=6.0 Hz); 7.91 (m, 4H, Ph-NO$_2$); 7.31 (s, 2H, Ph); 4.65 (d, 2H, CH$_2$, J=6.0 Hz); 3.83 (s, 6H, 2× OCH$_3$); 2.28 (s, 3H, CH$_3$).

3.3) 4-acetoxy-3,5-dimethoxy-N-[(4-aminophenyl)methyl]-benzamide:

The experimental protocol used is the same as that described for intermediate 2.2, 4-acetoxy-3,5-dimethoxy-N-[(4-nitrophenyl)methyl]-benzamide replacing the 3,5-bis-(1,1-dimethylethyl)-4-hydroxy-N-[(4-nitrophenyl)methyl]-benzamide. A colourless oil is obtained with a yield of 82%. The product is used directly in the following stage without additional purification.

3.4) 4-acetoxy-3,5-dimethoxy-N-{4-[[(2-thienyl (imino) methyl)amino]phenyl]methyl}-benzamide: 3

The experimental protocol used is the same as that described for compound 1, with 4-acetoxy-3,5-dimethoxy-N-[(4-aminophenyl)methyl]-benzamide replacing the 3,5-bis-(1,1-dimethylethyl)-4-hydroxy-N-(4-aminophenyl)-benzamide. The base 3 in the form of a beige powder is obtained with a yield of 65%. Melting point: 47–48° C.

NMR $^1$H (400 MHz, DMSO d6, δ): 9.08 (wide s, 1H, CONH); 7.75 (m, 1H, thiophene); 7.62 (m, 1H, thiophene); 7.30 (s, 2H, Ph); 7.10 (m, 1H, thiophene); 5 7.07 (m, 4H, Ph-N); 6.48 (wide s, 2H, NH$_2$); 4.50 (d, 2H, CH$_2$, J=4.6 Hz); 3.80 (s, 6H, 2× OCH$_3$); 2.30 (s, 3H, CH$_3$). IR: $v_{C=O}$ (ester): 1760 cm$^{-1}$; $v_{C=O}$ (amide): 1630 cm$^{-1}$; $v_{C=N}$ (amidine): 1540 cm$^{-1}$.

Example 4

3,5-dimethoxy-4-hydroxy-N-{4[[(2-thienyl(imino) methyl)amino]phenyl]methyl}-benzamide: 4

In a 50 ml flask, 1 ml (2 mmoles) of 2N hydrochloric acid is introduced dropwise into a solution of 0.59 g (1 mmole) of compound 3 in 5 ml of ethanol. The reaction medium is agitated for 18 hours at 50° C. The solvents are evaporated to dryness, the residue is taken up in dichloromethane (5 ml) and washed with molar soda solution (3×5 ml). After drying the organic phase, filtration and concentration to dryness is carried out and the oil obtained is purified by chromatography on a silica gel column (eluant: dichloromethane/methanol: 9/1). The pure fractions are collected and after evaporation under vacuum a beige powder is obtained with a yield of 60%. Melting point 55–58° C.

NMR $^1$H (400 MHz, DMSO d6, δ): 8.92 (s, 1H, OH); 8.84 (m, 1H, CONH); 7.75 (m, 1H, thiophene); 7.63 (m, 1H, thiophene); 7.26 (s, 2H, Ph); 7.10 (m, 1H, thiophene); 7.05 (m, 4H, Ph-N); 6.50 (s, 2H, NH$_2$); 4.45 (d, 2H, CH$_2$, J=5.7 Hz); 3.81 (s, 6H, 2× OCH$_3$). IR: $v_{OH}$: 3300 cm$^{-1}$; $v_{C=O}$ (amide): 1630 cm$^{-1}$; $v_{C=N}$ (amidine): 1590 cm$^{-1}$.

Example 5

3,5-bis-(1,1-dimethylethyl)-4-hydroxy-N-{4-[2-[(2-thienyl-(imino)methyl)amino]phenyl]ethyl}-benzamide hydriodide: 5

5.1) 3,5-bis-(1,1-dimethylethyl)-4-hydroxy-N-[2-(4-nitrophenyl)ethyl]-benzamide:

2.02 g (10 mmoles) of 4-nitrophenetylamine hydrochloride, 2.5 g (10 mmoles) of 3,5-di-tert-butyl-4-hydroxy-benzoic acid, 1.38 ml (10 mmoles) of triethylamine and 2.26 g (11 mmoles) of dicyclohexylcarbodiimide are introduced into a 100 ml flask containing 20 ml of THF. The reaction medium is agitated for 15 hours at ambient temperature, the precipitate which appears is filtered out and rinsed with ethyl acetate. After concentration of the filtrate under reduced pressure, the residue is precipitated from diethyl ether. The solid is recovered by filtration and rinsed with diethyl ether. A white powder is obtained with a yield of 73%. Melting point: 204–206° C.

NMR $^1$H (100 MHz, CDCl$_3$, δ): 7.52 (s, 2H, Ph); 6.85 (m, 4H, Ph-NO$_2$); 6.02 (m, 1H, NHCO); 3.62 (m, 2H, CH$_2$—NHCO); 2.82 (m, 2H, CH$_2$-Ph-NO$_2$); 1.48 (s, 18H, 2× tBu).

5.2) 3,5-bis-(1,1-dimethylethyl)-4-hydroxy-N-[2-(4-aminophenyl)ethyl]-benzamide:

The experimental protocol used is the same as that described for intermediate 2.2, 3,5-bis-(1,1-dimethylethyl)-4-hydroxy-N-[2-(4-nitrophenyl)ethyl]-benzamide replacing the 3,5-bis-(1,1-dimethylethyl)-4-hydroxy-N-[(4-nitrophenyl)methyl]-benzamide. A white powder is obtained with a yield of 76%. Melting point: 193–195° C.

NMR $^1$H (100 MHz, CDCl$_3$, δ): 7.80 (m, 4H, Ph-NH$_2$); 7.55 (s, 2H, Ph); 6.10 (m, 1H, NHCO); 5.55 (s, 1H, OH); 3.75 (m, 2H, CH$_2$—NHCO); 3.10 (m, 2H, CH$_2$-Ph-NH$_2$); 1.50 (s, 18H, 2× tBu).

5.3) 3,5-bis-(1,1-dimethylethyl)-4-hydroxy-N-{4-[2-[(2-thienyl(imino)methyl)-amino]phenyl]ethyl}-benzamide hydriodide: 5

0.78 g (2.74 mmoles) of S-methyl-2-thiophene-thiocarboximide hydriodide (Ann. *Chim.* (1962), 7, 303–337) is introduced into a 50 ml flask containing 1.01 g (2.74 mmoles) of 3,5-bis-(1,1-dimethylethyl)-4-hydroxy-N-[2-(4-aminophenyl)ethyl]-benzamide dissolved in 20 ml of 2-propanol. The reaction medium is heated at 40° C. for 4 hours. The solvent is evaporated off under vacuum and the residue is precipitated in the presence of 50 ml of a water/ethyl acetate mixture (1/1). The crystals formed are filtered out and washed successively with ethyl acetate and diethyl ether. After drying, a pale yellow powder is obtained with a yield of 68%. Melting point: 185–186° C.

NMR $^1$H (400 MHz, DMSO d6, δ): 9.80 (s, 1H, NH$^+$); 8.88 (s, 1H, NH$^+$); 8.40 (s, 1H, CONH); 8.12 (m, 2H, thiophene); 7.60 (s, 2H, Ph); 7.42 (m, 6H, thiophene, Ph-NH, OH); 3.52 (d, 2H, CH$_2$—NHCO, J=5.9 Hz); 2.90 (m, 2H, CH$_2$-Ph-NH); 1.40 (s, 18H, 2× tBu). IR: $v_{OH}$: 3624 cm$^{-1}$, 3423 cm$^{-1}$; $v_{C=O}$ (amide): 1636 cm$^{-1}$; $v_{C=N}$ (amidine): 1569 cm$^{-1}$.

Example 6

4-acetoxy-3,5-dimethoxy-N-{4-[2-[(2-thienyl(imino) methyl)-amino]phenyl]ethyl}-benzamide fumarate: 6

6.1) 4-acetoxy-3,5-dimethoxy-N-[2-(4-nitrophenyl)ethyl]-benzamide:

The experimental protocol used is the same as that described for intermediate 5.1, with 4-acetoxy-3,5-dimethoxy-benzoic acid (intermediate 3.1) replacing the 3,5-di-tert-butyl-4-hydroxy benzoic acid. A colourless oil is obtained with a yield of 70%. The product is used directly in the following stage.

6.2) 4-acetoxy-3,5-dimethoxy-N-[2-(4-aminophenyl)ethyl]-benzamide:

The experimental protocol used is the same as that described for intermediate 2.2, with 4-acetoxy-3,5-dimethoxy-N-[2-(4-nitrophenyl)ethyl]-benzamide replacing the 3,5-bis-(1,1-dimethylethyl)-4-hydroxy-N-[(4-nitrophenyl)methyl]-benzamide. A colourless oil is obtained with a quantitative yield. The product is used directly in the following stage without additional purification.

6.3) 4-acetoxy-3,5-dimethoxy-N-{4-[2-[(2-thienyl(imino)methyl)amino]-phenyl]ethyl}-benzamide fumarate: 6

The experimental protocol used to produce the free base is the same as that described for the synthesis of compound 1, with 4-acetoxy-3,5-dimethoxy-N-[2-(4-aminophenyl)ethyl]-benzamide replacing the 3,5-bis-(1,1-dimethylethyl)-4-hydroxy-N-(4-aminophenyl)-benzamide.

The product of the reaction is salified in the presence of an equimolar quantity of fumaric acid in ethanol under reflux. Compound 6 is obtained in the form of a beige powder with a yield of 74%. Melting point: 178–180° C.

NMR $^1$H (400 MHz, DMSO d6, δ): 8.60 (m, 1H, CONH); 7.75 (m, 1H, thiophene); 7.64 (d, 1H, thiophene, J=5.0 Hz); 7.20 (s, 2H, Ph); 7.11 (t, 1H, thiophene, J=9.0 Hz); 7.02 (m, 4H, Ph-N); 6.61 (s, 2H, CH=CH fumarate); 3.81 (s, 6H, 2× OCH$_3$); 3.50 (q, 2H, CH$_2$—N, J=6.5 Hz); 2.82 (t, CH$_2$-Ph, J=7.0 Hz); 2.27 (s, 3H, CH$_3$). IR: $\nu_{C=O}$ (ester): 1750 cm$^{-1}$; $\nu_{C=O}$ (amide): 1640 cm$^{-1}$; $\nu_{C=N}$ (amidine): 1550 cm$^{-1}$.

Example 7

3,5-dimethoxy-4-hydroxy-N-{4-[2-[(2-thienyl-(imino)methyl)-amino]phenyl]ethyl}-benzamide hydrochloride In a 50 ml flask, 1.40 ml (2.80 mmoles) of a solution of 2N hydrochloric acid is added dropwise to a solution of 0.64 g (1.37 mmoles) of compound 6 in the form of the free base in 5 ml of ethanol. The reaction medium is agitated for 18 hours at 50° C. The solvents are evaporated to dryness and the evaporation residue is precipitated from a mixture of 5 ml of a 2N solution of soda and 10 ml of dichloromethane. After filtration, the solid is taken up in (4N) hydrochloric ethanol. A light precipitate is then eliminated. The solvent is evaporated under reduced pressure and the residue taken up in acetone. Product 7 precipitated in the form of the hydrochloride is obtained with a yield of 58%. Melting point: 164–167° C.

NMR $^1$H (400 MHz, DMSO d6, δ): 9.80 (wide s, 1H, NH$^+$); 8.90 (s, 2H, NH$^+$, OH); 8.54 (m, 1H, CONH); 8.18 (s, 1H, thiophene); 8.16 (s, 1H, thiophene); 7.40 (m, 4H, Ph-N); 7.21 (s, 2H, Ph); 7.11 (m, 1H, thiophene); 3.81 (s, 6H, 2× OCH$_3$); 3.51 (q, 2H, CH$_2$—N, J=7.0 Hz); 2.92 (t, CH$_2$-Ph, J=7.0 Hz).

IR: $\nu_{OH}$: 3300 cm$^{-1}$; $\nu_{C=O}$ (amide): 1620 cm$^{-1}$; $\nu_{C=N}$ (amidine): 1560 cm$^{-1}$.

Example 8

3,4,5-trihydroxy-N-{4-[2-[(2-thienyl(imino)methyl)-amino]phenyl]ethyl}-benzamide hemi-fumarate: 8

8.1) 3,4,5-trihydroxy-N-[2-(4-nitrophenyl)ethyl]-benzamide:

2 g (11.5 mmoles) of gallic acid, 2.5 g (11.5 mmoles) of 4-nitrophenetylamine hydrochloride, 1.8 g (11.5 mmoles) of hydrated 1-hydroxybenzotriazole, 2.25 g (11.5 mmoles) of 1-(3-dimethylaminopropyl)-3-ethylcarbodiimide hydrochloride and 3.3 ml (23 mmoles) of triethylamine are introduced into a 100 ml flask containing 30 ml of anhydrous DMF. The orange-coloured solution obtained is agitated at 20° C. for 20 hours and diluted in a mixture of dichloromethane (50 ml) and water (30 ml). After decanting, the organic phase is washed with a molar solution of hydrochloric acid (20 ml) and with water (3×20 ml) until neutrality is achieved. After drying the organic phase over magnesium sulphate, followed by filtration and concentration under vacuum, the residue is purified on a silica gel column (eluant: dichloromethane/methanol: 9/1). The expected product is obtained in the form of a colourless oil with a yield of 42% (1.57 g).

NMR $^1$H (100 MHz, DMSO d6, δ): 8.95 (m, 3H, 3× OH); 7.85 (m, 4H, Ph-NO$_2$); 6.80 (s, 2H, Ph); 3.36 (m, 2H, CH$_2$-N); 2.97 (t, 2H, CH$_2$-Ph, J=6.0 Hz).

8.2) 3,4,5-trihydroxy-N-[2-(4-aminophenyl)ethyl]-benzamide:

The experimental protocol used is the same as that described for intermediate 2.2, with 3,4,5-trihydroxy-N-[2-(4-nitrophenyl)ethyl]-benzamide replacing the 3,5-bis-(1,1-dimethylethyl)-4-hydroxy-N-[(4-nitrophenyl)methyl]-benzamide. A beige powder is obtained with a yield of 89%. Melting point: 167–169° C.

NMR $^1$H (100 MHz, DMSO d6, δ): 8.80 (m, 3H, OH); 8.07 (t, 1H, NHCO, J=5.0 Hz); 6.81 (s, 2H, Ph); 6.68 (m, 4H, Ph-NH$_2$); 3.28 (m, 2H, CH$_2$-N); 2.60 (t, 2H, CH$_2$-Ph, J=7.0 Hz).

8.3) 3,4,5-trihydroxy-N-{4-[2-[(2-thienyl(imino)methyl)amino]-phenyl]ethyl}-benzamide hemi-fumarate: 8

The experimental protocol used is the same as that described for compound 1, with 3,4,5-trihydroxy-N-[2-(4-aminophenyl)ethyl]-benzamide replacing the 3,5-bis-(1,1-dimethylethyl)-4-hydroxy-N-(4-aminophenyl)-benzamide. Base 8 is obtained in the form of a powder which is salified, by heating under reflux with ethanol, in the presence of one equivalent of fumaric acid. The salt crystallizes spontaneously at 20° C. After filtration and washing with ethanol the expected product is obtained in the form of a beige powder with a yield of 53%. Melting point: 245–246° C.

NMR $^1$H (400 MHz, DMSO d6, δ): 8.85 (m, 3H, 3× OH); 8.14 (t, 1H, NHCO, J=5.0 Hz); 7.73 (s, 1H, thiophene); 7.60 (d, 1H, thiophene, J=5.0 Hz); 7.16 (s, 2H, Ph); 7.09 (t, 1H, thiophene, J=4.0 Hz); 6.80 (m, 4H, Ph-N); 6.59 (wide s, 2H, ½—CH=CH, NH); 3.41 (m, 3H, CH$_2$—N$^+$NH); 2.76 (t, 2H, CH$_2$, J=7.5 Hz). IR: $\nu_{OH}$: 3300 cm$^{-1}$; $\nu_{C=O}$ (amide): 1620 cm$^{-1}$; $\nu_{C=N}$ (amidine): 1590 cm$^{-1}$.

Example 9

N-{4-[4-[3,5-bis-(1,1-dimethylethyl)-4-hydroxybenzoyl]-1-piperazinyl]phenyl}-2-thiophenecarboximidamide hydrochloride: 9

9.1) 2,6-bis-(1,1-dimethylethyl)-4-{[4-(4-nitrophenyl)-1-piperazinyl]-carbonyl}-phenol:

2.07 g (10 mmoles) of 1-(4-nitrophenyl)piperazine, 2.5 g (10 mmoles) of 3,5-di-tert-butyl-4-hydroxybenzoic acid and 2.26 g (11 mmoles) of dicyclohexylcarbodiimide are introduced into a 100 ml flask containing 25 ml of DMF. The reaction medium is agitated for 15 hours at ambient temperature, the precipitate which appears is filtered out and rinsed with ethyl acetate. After concentration of the filtrate under reduced pressure, the residue is diluted in 20 ml of ethyl acetate and a new insoluble is eliminated by filtration. The solvent is evaporated off under vacuum and the residue is precipitated from diethyl ether. The solid is filtered, rinsed with 2×20 ml of ethyl acetate in order to obtain a yellow powder with a yield of 89%. Melting point: 159.5–160.5° C.

NMR $^1$H (100 MHz, CDCl$_3$, δ): 7.58 (m, 4H, Ph-NO$_2$); 7.30 (s, 2H, Ph); 5.50 (s, 1H, OH); 3.85 (m, 4H, piperazine); 3.55 (m, 4H, piperazine); 1.46 (s, 18H, 2× tBu).

9.2) 2,6-bis-(1,1-dimethylethyl)-4-{[4-(4-aminophenyl)-1-piperazinyl]-carbonyl}-phenol:

In a 250 ml Parr flask, 2.19 g (5.0 mmoles) of intermediate 9.1 is dissolved in 50 ml of absolute ethanol in the presence of 10% Pd/C. The mixture is agitated under 20 PSI of hydrogen, at 30° C., for one hour. After filtration on celite, the filtrate is concentrated under vacuum. The evaporation residue is taken up in 25 ml of diethyl ether, filtered and rinsed with 2×20 ml of diethyl ether. A pale pink powder is obtained with a yield of 82%. Melting point: 221–222° C.

NMR $^1$H (100 MHz, CDCl$_3$, δ): 7.30 (s, 2H, Ph); 6.75 (m, 4H, Ph-NH$_2$); 5.45 (s, 1H, OH); 3.80 (m, 4H, piperazine); 3.10 (m, 4H, piperazine); 1.49 (s, 18H, 2× tBu).

9.3) N-{4-[4-[3,5-bis-(1,1-dimethylethyl)-4-hydroxybenzoyl]-1-piperazinyl]-phenyl}-2-thiophenecarboximidamide hydrochloride: 9

The experimental protocol used is the same as that described for compound 1, with 2,6-bis-(1,1-dimethylethyl)-4-{[4-(4-aminophenyl)-1-piperazinyl]-carbonyl}-phenol replacing the 3,5-bis-(1,1-dimethylethyl)-4-hydroxy-N-(4-aminophenyl)-benzamide. After treatment with a molar solution of HCl in anhydrous diethyl ether, a beige powder is obtained with a yield of 75%. Melting point: 235–236° C.

NMR $^1$H (400 MHz, DMSO d6, δ): 11.45 (s, 1H, NH$^+$); 9.78 (s, 1H, NH$^+$); 8.75 (s, 1H, NH$^+$); 8.19 (m, 2H, thiophene); 7.29 (m, 5H, Ph-N, thiophene); 7.10 (s, 2H, Ph); 5.60 (wide s, 1H, OH); 3.70 (m, 4H, piperazine); 3.30 (m, 4H, piperazine); 1.40 (s, 18H, 2× tBu). IR: $v_{OH}$: 3633 cm$^{-1}$, 3433 cm$^{-1}$, $v_{C=O}$ (amide): 1617 cm$^{-1}$; $v_{C=N}$ (amidine): 1590 cm$^{-1}$.

Example 10

N-{4-[4-[3,5-bis-(1,1-dimethylethyl)-4-hydroxybenzyl]-1-piperazinyl]phenyl}-2-thiophenecarboximidamide hydrochloride: 10

10.1) 2,6-bis-(1,1-dimethylethyl)-4-bromomethylphenol:

In a 250 ml three-necked flask under a nitrogen atmosphere, 2.36 g (10 mmoles) of 3,5 di-tert-butyl-4-hydroxybenzylic alcohol is dissolved in 25 ml of anhydrous THF. The solution is cooled down using an ice bath before the dropwise addition of 0.95 ml (10 mmoles) of phosphorus tribromide diluted with 25 ml of anhydrous THF. After 15 minutes of agitation at 0° C., the solution is diluted with 100 ml of dichloromethane and washed with 3×30 ml of water followed by 30 ml of brine. The organic phase is dried over sodium sulphate, filtered and concentrated under vacuum to produce a brown oil which is used directly in the following stage.

10.2) 2,6-bis-(1,1-dimethylethyl)-4-{[4-(4-nitrophenyl)-1-piperazinyl]-methyl}-phenol:

In a 100 ml flask containing a solution of 2.99 g (10 mmoles) of 2,6-bis-(1,1-dimethylethyl)-4-bromomethylphenol in 30 ml of DMF, 1.38 g (10 mmoles) of potassium carbonate and 2.07 g (10 mmoles) of 1-(4-nitrophenyl)piperazine are added successively. After agitation for two hours at ambient temperature, the reaction medium is diluted with 150 ml of dichloromethane and washed successively with 3×40 ml of water followed by 40 ml of brine. The organic solution is dried over sodium sulphate, filtered and concentrated under reduced pressure. The brown residue obtained is purified on a silica gel column (eluant: petroleum ether (B.p. 40–70° C.)/ethyl acetate: 8/2). After concentration of the pure fractions, 2.31 g (54%) of a brown powder is obtained. Melting point: 177.5–178.5° C.

NMR $^1$H (100 MHz, CDCl$_3$, δ): 7.50 (m, 4H, Ph-NO$_2$); 7.12 (s, 2H, Ph); 5.19 (s, 1H, OH); 3.50 (s, 2H, CH$_2$-Ph); 3.49 (m, 4H, piperazine); 2.60 (m, 4H, piperazine); 1.49 (s, 18H, 2× tBu).

10.3) 2,6-bis-(1,1-dimethylethyl)-4-{[4-(4-aminophenyl)-1-piperazinyl]-methyl}-phenol:

The experimental protocol used is the same as that described for intermediate 9.2, with 2,6-bis-(1,1-dimethylethyl)-4-{[[4-(4-nitrophenyl)-1-piperazinyl]-carbonyl]-methyl}-phenol replacing the 2,6-bis-(1,1-dimethylethyl)-4-{[4-(4-nitrophenyl)- 1-piperazinyl]-carbonyl)}-phenol. A pale pink powder is obtained with a yield of 75%. Melting point: 152–154° C.

NMR $^1$H (100 MHz, CDCl$_3$, δ): 7.12 (s, 2H, Ph); 6.78 (m, 4H, Ph-NH$_2$); 3.59 (s, 2H, CH$_2$-Ph); 3.18 (m, 4H, piperazine); 2.70 (m, 4H, piperazine); 1.47 (s, 18H, 2× tBu).

10.4) N-{4-[4-[3,5-bis-(1,1-dimethylethyl)-4-hydroxybenzyl]-1-piperazinyl]-phenyl}-2-thiophenecarboximidamide hydrochloride: 10

0.43 g (1.5 mmole) of S-methyl-2-thiophenethiocarboximide hydriodide (*Ann. Chim.* (1962), 7, 303–337) is introduced into a 100 ml flask containing 0.59 g (1.5 mmole) of intermediate 10.3 in 20 ml of 2-propanol. After heating under reflux for 15 hours, the reaction medium is concentrated to dryness under vacuum. The residue is purified on a silica gel column (eluant: dichloromethane/ethanol: 90/10). The pure fractions are concentrated under vacuum and the evaporation residue is salified in the presence of a molar solution of HCl in anhydrous diethyl ether. A pale yellow powder is obtained with a yield of 40%. Melting point: 234–236° C.

NMR $^1$H (400 MHz, DMSO d6, δ): 11.60 (s, 1H, NH$^+$); 11.40 (s, 1H, NH$^+$); 9.75 (s, 1H, NH$^+$); 8.70 (s, 1H, NH$^+$); 8.17 (m, 2H, thiophene); 7.39 (s, 2H, Ph); 7.38 (m, 1H, thiophene); 7.24 (m, 5H, Ph-N, OH); 4.26 (d, 2H, CH$_2$-Ph, J=4.6 Hz); 3.90 (m, 2H, piperazine); 3.35 (m, 4H, piperazine); 3.15 (m, 2H, piperazine); 1.41 (s, 18H, 2× tBu). IR: $v_{OH}$: 3624 cm$^{-1}$, 3418 cm$^{-1}$; $v_{C=N}$ (amidine): 1610 cm$^{-1}$.

Example 11

N-{4-[4-[3,5-dimethoxy-4-hydroxybenzoyl]-1-piperazinyl]-phenyl}-2-thiophenecarboximidamide hydrochloride: 11

11.1) 2,6-dimethoxy-4-{[4-(4-nitrophenyl)-1-piperazinyl]carbonyl}-phenol:

In a 100 ml flask, 0.99 g (5 mmoles) of syringic acid, 0.74 g (5.5 mmoles) of hydroxybenzotriazol, 1.10 g (5.5 mmoles) of dicyclohexylcarbodiimide and 1.04 g (5 mmoles) of 1-(4-nitrophenyl)piperazine are dissolved in 10 ml of DMF. After agitation at ambient temperature for 7 hours, the mixture is filtered and the precipitate rinsed with 20 ml of DMF followed by 100 ml of chloroform. 2 g of a yellow powder is obtained, containing approximately 20% of dicyclohexylurea. The product is used as it is in the following stage.

NMR $^1$H (100 MHz, DMSO d6, δ): 7.69 (m, 4H, Ph-NO$_2$); 6.88 (s, 2H, Ph); 5.72 (m, 1H, OH); 3.91 (s, 6H, 2× OCH$_3$); 3.75 (m, 4H, piperazine); 3.49 (m, 4H, piperazine).

11.2) 2,6-dimethoxy-4-{[4-(4-aminophenyl)-1-piperazinyl]carbonyl}-phenol:

In a 250 ml Parr flask, 2 g of intermediate 11.1 is dissolved in 40 ml of absolute ethanol/DMSO (1/3) in the presence of 10% Pd/C. The mixture is agitated under 20 PSI of hydrogen, at 25° C., for 15 hours. After filtration on celite, the filtrate is concentrated under vacuum. The brown evaporation residue is taken up in 50 ml of ethyl acetate, the precipitate formed is eliminated by filtration, rinsed with 20 ml of ethyl acetate and the filtrate extracted with 2×25 ml of a molar solution of HCl. The aqueous phase is alkalinized by the addition of powdered sodium carbonate and extracted with 2×50 ml of ethyl acetate. The organic solution is dried over sodium sulphate, filtered and concentrated under vacuum. The powder obtained is taken up in 20 ml of diethyl ether containing 3 ml of methanol, filtered and rinsed using diethyl ether. 400 mg (22% over the two stages) of brown crystals are obtained. Melting point: 182–183° C.

NMR $^1$H (100 MHz, DMSO d6, δ): 6.80 (s, 2H, Ph); 6.74 (m, 4H, Ph-NH$_2$); 4.80 (m, 2H, NH$_2$); 3.91 (s, 6H, 2× OCH$_3$); 3.77 (m, 4H, piperazine); 3.08 (m, 4H, piperazine).

11.3) N-{4-[4-[3,5-dimethoxy-4-hydroxybenzoyl]-1-piperazinyl]-phenyl}-2-thiophenecarboximidamide hydrochloride: 11

0.32 g (1.13 mmole) of S-methyl-2-thiophenethiocarboximide hydriodide (*Ann. Chim.* (1962), 7, 303–337) is introduced into a 100 ml flask containing a solution of 0.4 g (1.13 mmole) of intermediate 11.2 in 10 ml of 2-propanol. After heating at 50° C. for 15 hours, the reaction medium is concentrated to dryness under vacuum. The evaporation residue is then taken up in 100 ml of an ethyl acetate/saturated solution of sodium carbonate mixture (1/1). A precipitate appears which is filtered and rinsed successively with 20 ml of water, 20 ml of ethyl acetate and 50 ml of ether. The base obtained is salified in the presence of a molar solution of HCl in anhydrous diethyl ether. After filtration, rinsing with 10 ml of acetone and drying, 0.12 g (20%) of a pale yellow powder is obtained. Melting point: 184–185° C.

NMR $^1$H (400 MHz, DMSO d6, δ): 11.47 (s, 1H, NH$^+$); 9.78 (s, 1H, NH$^+$); 8.76 (s, 1H, NH$^+$); 8.18 (m, 2H, thiophene); 7.37 (m, 1H, thiophene); 7.28 (m, 4H, Ph-N); 6.74 (s, 2H, Ph); 4.27 (wide s, 1H, OH); 3.80 (s, 6H, 2× OCH$_3$); 3.70 (m, 4H, piperazine); 3.33 (m, 4H, piperazine). IR: $v_{OH}$: 3423 cm$^{-1}$; $v_{C=O}$ (amide): 1610 cm$^{-1}$; $v_{C=N}$ (amidine): 1587 cm$^{-1}$.

Example 12

3,4-dihydro-6-hydroxy-2,5,7,8-tetramethyl-N-{4-[(2-thienyl (imino)methyl)amino]phenyl}-2H-1-benzopyran-2-carboxamide hydrochloride: 12

12.1) 3,4-dihydro-6-hydroxy-2,5,7,8-tetramethyl-N-(4-nitrophenyl)-2H-1-benzopyran-2-carboxamide:

In a 100 ml flask, 1.62 g (10 mmoles) of 1.1'-carbonyldiimidazol is added to a solution of 2.5 g (10 mmoles) of Trolox® in 25 ml of THF. After agitation at ambient temperature for one hour, a solution of 4-nitroaniline in 20 ml of THF is added dropwise. Agitation is continued for 15 hours and the solvent is evaporated off under vacuum. The residue is diluted in 50 ml of dichloromethane and washed successively with 25 ml of a molar solution of hydrochloric acid, 25 ml of water and 25 ml of brine. The organic phase is dried over sodium sulphate, filtered and concentrated under reduced pressure. The oil obtained is purified on a silica gel column (eluant: petroleum ether (B.p. 40–70° C.)/ethyl acetate: 7/3). After concentration of the pure fractions, a pale yellow powder is obtained with a yield of 77%. Melting point: 150–151° C.

NMR $^1$H (100 MHz, CDCl$_3$, δ): 8.68 (s, 1H, CONH); 7.91 (m, 4H, Ph); 4.59 (s, 1H, OH); 2.95–0.87 (m, 16H, Trolox®).

12.2) 3,4-dihydro-6-hydroxy-2,5,7,8-tetramethyl-N-(4-aminophenyl)-2H-1-benzopyran-2-carboxamide:

The experimental protocol used is the same as that described for intermediate 9.2, with 3,4-dihydro-6-hydroxy-2,5,7,8-tetramethyl-N-(4-nitrophenyl)-2H-1-benzopyran-2-carboxamide replacing the 2,6-bis-(1,1-dimethylethyl)-4-{[4-(4-nitrophenyl)-1-piperazinyl]-carbonyl}-phenol. The product of the reaction is purified on a silica gel column (eluant: petroleum ether (B.p. 40–70° C.)/ethyl acetate: 6/4). The pure fractions are collected, after evaporation of the solvent under vacuum, a colourless oil is obtained with a yield of 45%.

NMR $^1$H (100 MHz, CDCl$_3$, δ): 8.19 (s,1H, CONH); 7.00 (m, 4H, Ph); 4.59 (s, 1H, OH); 3.65 (wide s, 2H, NH$_2$); 2.95–0.87 (m, 16H, Trolox®).

12.3) 3,4-dihydro-6-hydroxy-2,5,7,8-tetramethyl-N-{4-[2-thienyl (iminomethyl)amino]phenyl}-2H-1-benzopyran-2-carboxamide hydrochloride: 12

The experimental protocol used is the same as that described for compound 1, with 3,4-dihydro-6-hydroxy-2,5,7,8-tetramethyl-N-(4-aminophenyl)-2H-1-benzopyran-2-carboxamide replacing the 3,5-bis-(1,1-dimethylethyl)-4-hydroxy-N-(4-aminophenyl)-benzamide. Melting point: 279–280° C.

NMR $^1$H (400 MHz, DMSO d6, δ): 9.80 (s, 1H, NH$^+$); 9.50 (s, 1H, NH$^+$); 8.73 (s, 1H, NHCO); 8.18 (m, 2H, thiophene); 7.60 (s, 1H, OH); 7.59 (m, 4H, Ph); 7.36 (m, 1H, thiophene); 2.60–1.57 (m, 16H, Trolox®). IR: $v_{OH}$: 3236 cm$^{-1}$; $v_{C=O}$ (amide): 1683 cm$^{-1}$; $v_{C=N}$ (amidine): 1577 cm$^{-1}$.

Example 13

N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide hydrochloride: 13

13.1) 3,4-dihydro-2,5,7,8-tetramethyl-2-{4-[(4-nitrophenyl)-1-piperazinyl]-carbonyl}-2H-1-benzopyran-6-ol:

In a 100 ml flask, 1.62 g (10 mmoles) of 1.1'-carbonyldiimidazole is added to a solution of 2.5 g (10 mmoles) of Trolox® in 25 ml of THF. After one hour of agitation at ambient temperature, a solution of 1-(4-nitrophenyl) piperazine in 10 ml of DMF is added dropwise. Agitation is continued for 15 hours, the reaction medium is then concentrated under vacuum. The evaporation residue is dissolved in 50 ml of dichloromethane and washed successively with 3×25 ml of water and 25 ml of brine. The organic phase is dried over sodium sulphate, filtered and concentrated under reduced pressure. The oil obtained is precipitated from 30 ml of a (95/5) ethyl acetate/methanol mixture, the solid is filtered out and washed with 2×20 ml of ethyl acetate. A pale yellow powder is obtained with a yield of 79%. Melting point: 199–200° C.

NMR $^1$H (100 MHz, CDCl$_3$, δ): 7.45 (m, 4H, Ph); 4.41–3.35 (m, 8H, piperazine); 2.95–1.25 (m, 16H, Trolox®).

13.2) 3,4-dihydro-2,5,7,8-tetramethyl-2-{4-[(4-aminophenyl)-1-piperazinyl]-carbonyl}-2H-1-benzopyran-6-ol:

The experimental protocol used is the same as that described for intermediate 2.2, with 3,4-dihydro-2,5,7,8-tetramethyl-2-{4-[(4-nitrophenyl)-1-piperazinyl]-carbonyl}-2H-1-benzopyran-6-ol replacing the 3,5-bis-(1,1-dimethylethyl)- 4-hydroxy-N-[(4-nitrophenyl)methyl]-benzamide. The product of the reaction is purified on a silica gel column (eluant: dichloromethane/methanol: 9/1). The pure fractions are collected to produce, after evaporation of the solvent under vacuum, a brown oil with a yield of 66%.

NMR $^1$H (100 MHz, CDCl$_3$, δ): 6.70 (m, 4H, Ph); 4.15–2.97 (m, 8H, piperazine); 2.80–0.90 (m, 18H, Trolox®).

13.3) N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide hydrochloride: 13

The experimental protocol used is the same as that described for the compound 1, with 3,4-dihydro-2,5,7,8-tetramethyl-2-{4-[(4-aminophenyl)-1-piperazinyl]-carbonyl}-2H-1-benzopyran-6-ol replacing the 3,5-bis-(1,1-dimethylethyl)-4-hydroxy-N-(4-amino-phenyl)-benzamide. However, the reaction is slower and requires 15 hours of heating. The base obtained after extraction is purified on a silica gel column (eluant: petroleum ether (B.p. 40–70° C.)/ethyl acetate: 3/7). The pure fractions are concentrated under vacuum and the evaporation residue is salified in the presence of a molar solution of HCl in anhydrous diethyl ether. A yellow powder pale is obtained with a yield of 40%. Melting point: 210–211° C.

NMR $^1$H (400 MHz, DMSO d6, δ): 11.50 (s, 1H, NH$^+$); 9.79 (s, 1H, NH$^+$); 8.69 (s, 1H, NH$^+$); 8.19 (m, 2H, thiophene); 7.38 (m, 1H, thiophene); 7.20 (m, 4H, Ph); 4.58 (wide s, 1H, OH); 4.11 (m, 2H, piperazine); 3.61 (m, 2H, piperazine); 3.19 (m, 4H, piperazine); 2.62–1.55 (m, 16H, Trolox®). IR: $v_{OH}$: 3410 cm$^{-1}$; $v_{C=O}$ (amide): 1642 cm$^{-1}$; $v_{C=N}$ (amidine): 1613 cm$^{-1}$.

Example 14

N-{4-[4-[(5 methoxy-1H-indol-3-yl)methylcarbonyl]-1-piperazinyl]phenyl}-2-thiophenecarboximidamide: 14

14.1) 1-[(5-methoxy-1H-indol-3-yl)methylcarbonyl]-4-(4-nitrophenyl)piperazine:

In a 100 ml flask, 1.62 g (10 mmoles) of 1.1'-carbonyldiimidazole is added to a solution of 2.05 g (10 mmoles) of 5-methoxyindole-3-acetic acid in 10 ml of THF. After one hour of agitation at ambient temperature, a solution of 1-(4-nitrophenyl)piperazine in 10 ml of DMF is added dropwise. Agitation is continued for 15 hours. The reaction medium is then concentrated under vacuum and the evaporation residue is precipitated from 50 ml of an ethyl acetate/water mixture (1/1). After filtration, the solid is rinsed successively with 50 ml of water, 50 ml of ethyl acetate and 50 ml of dichloromethane. After drying under vacuum, a yellow powder is obtained with a yield of 91%. Melting point: 239–240° C.

NMR $^1$H (100 MHz, DMSO d6, δ): 10.90 (m, 1H, NH); 7.63 (m, 4H, Ph-NO$_2$); 7.40–7.15 (m, 3H, indol); 6.87 (dd, 1H indol, $J_{ortho}$=8.7 Hz, $J_{meta}$=2.8 Hz); 3.90 (s, 2H, CH$_2$—CO); 3.88 (s, 3H, OCH$_3$); 3.79 (m, 4H, piperazine); 3.50 (m, 4H, piperazine).

14.2) 1-[(5 methoxy-1H-indol-3-yl)methylcarbonyl]-4-(4-aminophenyl)-piperazine:

In a 250 ml Parr flask, 1 g (2.53 mmoles) of intermediate 14.1 is dissolved in 30 ml of DMSO in the presence of 10% Pd/C. The mixture is agitated under 20 PSI of hydrogen, at 25° C., for 7 hours. After filtration on celite, the filtrate is concentrated under vacuum. The evaporation residue is diluted in 50 ml of ethyl acetate and washed with 3×50 ml of water. The organic phase is then extracted with 2×25 ml of a molar solution of HCl. After the acid solution is washed with 2×25 ml of ethyl acetate, it is alkalinized using sodium carbonate in powder form. Once the product is re-extracted using 2×50 ml of ethyl acetate, the organic solution is dried over sodium sulphate, filtered and the solvent is evaporated off under vacuum. The residue is purified on a silica gel column (eluant: dichloromethane/methanol: 98/2). The pure fractions are collected and after evaporation of the solvent under reduced pressure, 0.39 g of a pale yellow powder is obtained with a yield of 46%. Melting point: 119–120° C.

NMR $^1$H (100 MHz, CDCl$_3$, δ): 8.32 (s, 1H, indolic NH); 7.27–6.80 (m, 4H, indole); 6.69 (m, 4H, Ph-NH$_2$); 3.82 (s, 3H, OCH$_3$); 3.80 (s, 2H, CH$_2$—CO); 3.80 (m, 2H, piperazine); 3.62 (m, 2H, piperazine); 3.48 (s, 2H, NH$_2$); 2.90 (m, 4H, piperazine).

14.3) N-{4-[4-[(5 methoxy-1H-indole-3-yl)methylcarbonyl]-1-piperazinyl]phenyl}-2-thiophenecarboximidamide: 14

The experimental protocol used is the same as that described for the compound 1, with 1-[(5 methoxy-1H-indole-3-yl)methylcarbonyl]-4-(4-aminophenyl)-piperazine replacing the 3,5-bis-(1,1-dimethylethyl)-4-hydroxy-N-(4-aminophenyl)-benzamide. The expected product is isolated in the form of the free base with a yield of 20% (pale yellow powder). Melting point: 221–222° C.

NMR $^1$H (400 MHz, DMSO d6, δ): 10.78 (s, 1H, indolic NH); 7.72 (m, 1H, thiophene); 7.59 (m, 1H, thiophene); 7.22 (d, 1H, indole, J=8.7 Hz);
7.19 (m, 1H, thiophene); 7.09 (m, 2H, indole); 6.82 (m, 4H, Ph); 6.72 (m, 1H indole); 6.35 (s, 2H, NH$_2$); 3.80 (s, 2H, CH$_2$); 3.73 (s, 3H, CH$_3$); 3.62 (m, 4H, piperazine); 2.95 (m, 4H, piperazine). IR: $\nu_{OH}$: 3414 cm$^{-1}$; $\nu_{C=O}$ (amide): 1628 cm$^{-1}$; $\nu_{C=N}$ (amidine): 1590 cm$^{-1}$.

Example 15

N-[4-[4-[{3-[3,5-bis-(1,1-dimethylethyl)-4-hydroxyphenyl]-1-oxo-2-propenyl}-1-piperazinyl]-phenyl]]-2-thiophenecarboximidamide fumarate: 15

15.1) 2,6-bis-(1,1-dimethylethyl)-4-{3-[4-(4-nitrophenyl)-1-piperazinyl]-3-oxo-2-propenyl}-phenol:

The experimental protocol used is the same as that described for intermediate 11.1, with 3,5-di-tert-butyl-4-hydroxycinnamic acid replacing the syringic acid. An oil is obtained with a yield of 60%.

NMR $^1$H (100 MHz, CDCl$_3$, δ): 7.71 (d, 1H, C=CH, J=15.0 Hz); 7.51 (m, 4H, Ph-NO$_2$); 7.38 (s, 2H, Ph); 6.69 (d, 1H, HC=C, J=15.0 Hz); 5.50 (s, 1H, OH); 3.88 (m, 4H, piperazine); 3.53 (m, 4H, piperazine); 1.47 (s, 18H, 2× tBu).

15.2) 2,6-bis-(1,1-dimethylethyl)-4-{3-[4-(4-aminophenyl)-1-piperazinyl]-3-oxo-2-propenyl}-phenol:

In a 50 ml flask equipped with a refrigerant, 0.5 g (1 mmole) of intermediate 15.1 is dissolved in 5 ml of concentrated hydrochloric acid and 5 ml of absolute ethanol. The mixture is cooled down to 0° C. and 1.69 g (7.5 mmoles) of tin chloride (dihydrate) is added in several portions. After this addition, the reaction medium is heated under reflux for 30 minutes. The solvents are then evaporated off under vacuum, the residue is taken up in 15 ml of water, neutralized with 2N soda and diluted with 20 ml of dichloromethane. The precipitate obtained is filtered on celite and the filtrate is decanted. The organic phase is dried over sodium sulphate, filtered and concentrated under reduced pressure to produce 0.3 g (67%) of a yellow oil.

NMR $^1$H (100 MHz, CDCl$_3$, δ): 7.66 (d, 1H, C=CH, J=15.0 Hz); 7.37 (s, 2H, Ph); 6.75 (m, 4H, Ph-NH$_2$); 6.30 (d, 1H, HC=C, J=15.0 Hz); 5.46 (s, 1H, OH); 3.80 (m, 4H, piperazine); 3.06 (m, 4H, piperazine); 1.46 (s, 18H, 2× tBu).

15.3) N-[4-[4-[{3-[3,5-bis-(1,1-dimethylethyl)-4-hydroxyphenyl]-1-oxo-2-propenyl}-1-piperazinyl]-phenyl]]-2-thiophenecarboximidamide fumarate: 15

The experimental protocol used is the same as that described for compound 1, with 2,6-bis-(1,1-dimethylethyl)-4-{3-[4-(4-aminophenyl)-1-piperazinyl]-3-oxo-2-propenyl}-phenol replacing the 3,5-bis-(1,1-dimethylethyl)-4-hydroxy-N-(4-aminophenyl)-benzamide.

The product of the reaction is salified in the presence of an equimolar quantity of fumaric acid in ethanol under reflux. Compound 15 is obtained in the form of a yellow powder with a yield of 22%. Melting point: 170.5–173° C.

NMR $^1$H (400 MHz, DMSO d6, δ): 7.77 (s, 1H, thiophene); 7.67 (d, 1H, thiophene, J=5.0 Hz); 7.48 (d, 1H, C=CH, J=15.0 Hz); 7.39 (s, 2H, Ph); 7.34 (wide s, 1H, OH); 7.13 (t, 1H, thiophene, J=4.0 Hz); 7.05 (d, 1H, HC=C, J=15.0 Hz); 6.92 (m, 4H, Ph-N); 6.60 (s, 2H, CH=CH fumarate); 3.78 (m, 4H, piperazine); 3.13 (m, 4H, piperazine); 1.41 (s, 18H, 2× tBu). IR: $\nu_{OH}$: 3619 cm$^{-1}$, 3300 cm$^{-1}$; $\nu_{C=}$(amide): 1640 cm$^{-1}$; $\nu_{C=C}$: 1600 cm$^{-1}$; $\nu_{C=N}$ (amidine): 1570 cm$^{-1}$.

Example 16

3,5-bis-(1,1-dimethylethyl)-4-hydroxy-N-{3-[[(2-thienyl-(imino)methyl)amino]phenyl]methyl}-benzamide hydrochloride: 16

16.1) 3,5-bis-(1,1-dimethylethyl)-4-hydroxy-N-[(3-nitrophenyl)methyl]-benzamide:

The experimental protocol used is the same as that described for intermediate 2.1, with 3-nitrobenzylamine hydrochloride replacing the 4-nitrobenzylamine hydrochloride. A white powder is obtained with a yield of 63%. Melting point: 210–211° C.

NMR $^1$H (100 MHz, DMSO, δ): 9.12 (m, 1H, NH); 8.25 (m, 2H, Ph-NO$_2$); 7.80 (m, 4H, Ph-NO$_2$ +Ph-OH); 7.60 (wide s, 1H, OH); 4.68 (d, 2H, CH$_2$, J=6 Hz); 1.55 (s, 18H, 2xtBu).

16.2) 3,5-bis-(1,1-dimethylethyl)-4-hydroxy-N-[(3-aminophenyl)methyl]-benzamide:

In a 250 ml Parr flask, 2.40 g (6.2 mmoles) of 3,5-bis-(1,1-dimethylethyl)-4-hydroxy-N-[(3-nitrophenyl)methyl]-benzamide is dissolved in 45 ml of an absolute ethanol/THF mixture (1/2) in the presence of 10% Pd/C. The mixture is agitated under 20 PSI of hydrogen, at 30° C., for three hours. After filtration on celite, the filtrate is concentrated to dryness and the residue is purified on a silica column (eluant: heptane/ethyl acetate: 60/40). The pure fractions are collected and concentrated under reduced pressure to produce 0.94 g (45%) of a white powder. Melting point: 171–172° C.

NMR $^1$H (100 MHz, CDCl$_3$, δ): 7.20 (m, 2H, Ph-NH$_2$); 6.70 (m, 4H, Ph-NH$_2$+Ph-OH); 6.34 (m, 1H, NH); 5.55 (s, 1H, OH); 4.56 (d, 2H, CH$_2$, J=6 Hz); 3.70 (wide s, 2H, NH$_2$); 1.49 (s, 18H, 2xtBu).

16.3) 3,5-bis-(1,1-dimethylethyl)-4-hydroxy-N-{3-[[(2-thienyl(imino)methyl)-amino]phenyl]methyl}-benzamide hydrochloride: 16

The experimental protocol used is the same as that described for compound 1, with 3,5-bis-(1,1-dimethylethyl)-4-hydroxy-N-[(3-aminophenyl)methyl]-benzamide replacing the 3,5-bis-(1,1-dimethylethyl)-4-hydroxy-N-(4-aminophenyl)-benzamide. After salification with a molar solution of HCl in an acetone/anhydrous methanol mixture, a pale yellow powder is obtained with a yield of 50%. Melting point: 226–227° C.

NMR $^1$H (400 MHz, DMSO d6, δ): 11.71 (s, 1H, NH$^+$); 9.93 (s, 1H, NH$^+$); 9.10 (s, 1H, CONH); 9.00 (s, 1H, NH$^+$); 8.18 (m, 2H, thiophene); 7.70 (s, 2H, Ph); 7.42 (m, 6H, thiophene, Ph-NH, OH); 4.50 (d, 2H, CH$_2$—NHCO, J=5.4 Hz); 1.40 (s, 18H, 2xtBu). IR: $v_{OH}$: 3420 cm$^{-1}$; $v_{C=O}$ (amide): 1639 cm$^{-1}$; $v_{C=N}$ (amidine): 1578 cm$^{-1}$.

Example 17

N-[3,5-bis-(1,1-dimethylethyl)-4-hydroxyphenyl]-N'-{{4-[(2-thienyl(imino)methyl)amino]phenyl}methyl}-urea hydrochloride: 17

17.1) 4-amino-2,6-bis-(1,1-dimethylethyl)-phenol:

In a 250 ml Parr flask, 3.6 g (14 mmoles) of 4-nitro-2,6-bis-(1,1-dimethylethyl)-phenol (*J. Org. Chem.* (1968), 33 (1), 223–226) is dissolved in 60 ml of a (2/1) mixture of ethanol and dichloromethane in the presence of a catalytic quantity of 10% Pd/C. The mixture is agitated for 2 hours, at 20° C., under 20 PSI of hydrogen. After filtration on celite, the filtrate is concentrated to dryness under reduced pressure. The reddish-brown powder obtained is suspended in heptane (30 ml), filtered and rinsed with the same volume of heptane. The expected product is obtained in the form of an salmon pink powder with a yield of 50% (1.56 g). Melting point: 123–124° C.

NMR $^1$H (100 MHz, CDCl$_3$, δ): 6.60 (s, 2H, Ph); 4.65 (wide s, 1H, OH); 3.15 (wide s, 2H, NH$_2$); 1.42 (s, 18H, 2× tBu).

17.2) 4-nitrophenylacetic acid chloride:

3.75 ml (7.5 mmoles) of a 2M solution of oxalyl chloride in dichloromethane is added at 20° C. to a solution of 0.9 g (5 mmoles) of 4-nitrophenylacetic acid in a mixture composed of 10 ml of dichloromethane and 0.5 ml of DMF. After agitation for 30 minutes, the solution is concentrated under vacuum. The yellow oil obtained is used without additional purification in the following stage.

17.3) 4-nitrobenzylisocyanate:

The chloride of 4-nitrophenylacetic acid in solution in dry acetone (7.5 ml) is slowly added to an aqueous solution of 0.75 g (11.5 mmoles) of sodium azide, cooled down to 0° C. Agitation of the medium is maintained for one hour after the addition is completed, at 0–5° C. The reaction medium is then diluted with 30 ml of chloroform, decanted and the organic phase washed with water (20 ml) followed by a saturated solution of sodium chloride (20 ml). After drying over sodium sulphate, the organic solution is filtered and partly concentrated (≈20 ml) under vacuum. This solution of the acylazide in chloroform is then heated, under reflux, for one hour. The isocyanate obtained is used directly, in solution, in the following stage.

17.4) N-[3,5-bis-(1,1-dimethylethyl)-4-hydroxyphenyl]-N'-[(4-nitrophenyl)methyl]-urea:

1.1 g (5 mmoles) of 4-amino-2,6-bis-(1,1-dimethylethyl)-phenol is added in one portion to the isocyanate solution (intermediate 17.3) (theoretically 5 mmoles) in 20 ml of chloroform. After agitation for 2 hours at 20° C., the precipitate which appears is filtered out and rinsed with chloroform (2×20 ml). A yellow powder is obtained with a yield of 72%. Melting point: 240–241° C.

NMR $^1$H (100 MHz, DMSO d6, δ): 8.60 (s, 1H, NH-Ph); 8.01 (m, 4H, Ph-NO$_2$); 7.30 (s, 2H, Ph-OH); 6.77 (m, 1H, NH—CH$_2$); 6.71 (s, 1H, OH); 4.52 (d, 2H, CH$_2$, J=5.5 Hz); 1.49 (s, 18H, 2× tBu).

17.5) N-[(4-aminophenyl)methyl]-N'-[3,5-bis-(1,1-dimethylethyl)-4-hydroxyphenyl]-urea:

In a 100 ml autoclave, 0.55 g (1.38 mmole) of N-[3,5-bis-(1,1-dimethylethyl)-4-hydroxyphenyl]-N'-[(4-nitrophenyl)methyl]-urea is dissolved in a 2/1 mixture of ethanol and ethyl acetate, in the presence of 10% Pd/C. After hydrogenation for one and a half hours at 20° C., under 20 PSI, the mixture is filtered on celite and the filtrate is concentrated under vacuum. The evaporation residue is diluted in 20 ml of diethyl ether and the expected product crystallizes spontaneously. The crystals are filtered out and rinsed with 20 ml of diethyl ether. A white powder is obtained with a yield of 60% (0.31 g). Melting point: 194–195° C.

NMR $^1$H (100 MHz, CDCl$_3$, δ): 7.08 (s, 2H, Ph-OH); 6.87 (m, 4H, Ph-NH$_2$); 6.15 (s, 1H, NH-Ph); 5.14 (s, 1H, OH); 4.89 (m, 1H, NH—CH$_2$); 4.41 (d, 2H, CH$_2$, J=5.5 Hz); 3.65 (wide s, 2H, NH$_2$); 1.40 (s, 18H, 2× tBu).

17.6) N-[3,5-bis-(1,1-dimethylethyl)-4-hydroxyphenyl]-N'-{{4-[2-thienyl(imino-methyl)amino]phenyl}methyl}-urea hydrochloride: 17

The experimental protocol used is the same as that described for compound 1, with N-[(4-aminophenyl)methyl]-N'-[3,5-bis-(1,1-dimethylethyl)-4-hydroxyphenyl]-urea replacing the 3,5-bis-(1,1-dimethylethyl)-4-hydroxy-N-(4-aminophenyl)-benzamide. After salification with a molar solution of HCl in anhydrous diethyl ether, a white powder is obtained with a yield of 45%. Melting point: 236–237° C.

NMR $^1$H (400 MHz, DMSO d6, δ): 11.42 (wide s, 1H, NH$^+$); 9.77 (wide s, 1H, NH$^+$); 8.92 (wide s, 1H, NH$^+$); 8.54 (s, 1H, NH-Ph); 8.11 (m, 2H, thiophene); 7.41 (m, 5H, Ph-N, thiophene); 7.19 (s, 2H, Ph); 6.70 (m, 1H, NH—CH$_2$); 6.60 (s, 1H, OH); 4.35 (d, 2H, CH$_2$, J=5.5 Hz); 1.34 (s, 18H, 2× tBu). IR: $v_{OH}$: 3624 cm$^{-1}$; $v_{C=O}$ (urea): 1644 cm$^{-1}$; $v_{C=N}$ (amidine): 1569 cm$^{-1}$.

Example 18

N-[5-[{3-(3,5-bis-(1,1-dimethylethyl)-4-hydroxyphenyl)-1-oxo-2-propenyl}-amino]-2-hydroxyphenyl]-2-thiophenecarboximidamide hydrochloride: 18

18.1) 3-[(3,5-bis-(1,1-dimethylethyl)-4-hydroxyphenyl)-N-(4-hydroxy-3-nitrophenyl)-2-propenamide:

1.78 g (6.4 mmoles) of 3,5-di-tert-butyl-4-hydroxycinnamic acid, 0.99 g (6.4 mmoles) of 4-amino-2-nitrophenol, previously diluted in 10 ml of DMF, 0.86 g (6.4 mmoles) of hydroxybenzotriazol and 1.32 g (6.4 mmoles) of dicyclohexylcarbodiimide are introduced into a 50 ml flask containing 10 ml of THF. The reaction medium is agitated for 15 hours at ambient temperature, the precipitate which appears is filtered and rinsed with ethyl acetate. After concentration of the solution under reduced pressure, the residue is diluted in 20 ml of ethyl acetate and the insoluble part is filtered again. The filtrate is washed with 20 ml of a saturated solution of sodium carbonate followed by 20 ml of water and 20 ml of a saturated solution of sodium chloride. After drying over sodium sulphate, the organic solution is filtered and concentrated to dryness under reduced pressure. The residue is purified on a silica column (eluant: heptane/ethyl acetate: 8/2). The pure fractions are collected and concentrated under vacuum to produce 1.95 g (47%) of the expected compound in the form of a yellow-orange powder. Melting point: 231–232° C.

NMR $^1$H (100 MHz, CDCl$_3$, δ): 10.45 (s, 1H, NH); 8.45 (d, 1H, Ph-NO$_2$, J=1.7 Hz); 7.98 (dd, 1H, Ph-NO$_2$, J=1.7 Hz and J=6.8 Hz); 7.78 (d, 1H, —CH═CH—, J=10.5 Hz); 7.75 (s, 1H, OH); 7.40 (s, 2H, Ph-OH); 7.20 (d, 1H, Ph-NO$_2$); 6.48 (d, 1H, —H═CH—); 5.51 (s, 1H, OH); 1.50 (s, 18H, 2×tBu).

18.2) 3-[(3,5-bis-(1,1-dimethylethyl)-4-hydroxyphenyl]-N-(4-hydroxy-3-aminophenyl)-2-propenamide:

In a 100 ml flask equipped with a refrigerant, 0.9 g (2.18 mmoles) of 3-[(3,5-bis-(1,1-dimethylethyl)-4-hydroxyphenyl]-N-(4-hydroxy-3-nitrophenyl)-2-propenamide is dissolved in 20 ml of ethyl acetate, 2.46 g (10.9 mmoles) of tin chloride (dihydrate) is added and the mixture is heated at 70° C. for three hours. After returning to ambient temperature, the reaction medium is poured onto an agitated solution of sodium bicarbonate (0.1 M), a precipitate forms, which is eliminated by filtration on celite. The filtrate is decanted and the aqueous phase is extracted with 20 ml of ethyl acetate. The organic phases are collected together and washed with 20 ml of water followed by 20 ml of a saturated solution of sodium chloride. After drying over sodium sulphate and filtration, the organic solution is concentrated to dryness, under partial vacuum. The evaporation residue is suspended in a heptane/ethyl acetate mixture (1/1) and filtered to produce a yellowish powder with a yield of 53%. The product is used as it is in the following stage.

18.3) N-[5-[{3-(3,5-bis-(1,1-dimethylethyl)-4-hydroxyphenyl)-1-oxo-2-propenyl}amino]-2-hydroxyphenyl]-2-thiophenecarboximidamide hydrochloride: 18

The experimental protocol used is the same as that described for compound 1, with 3-[(3,5-bis-(1,1-dimethylethyl)-4-hydroxyphenyl]-N-(4-hydroxy-3-aminophenyl)-2-propenamide replacing the 3,5-bis-(1,1-dimethylethyl)-4-hydroxy-N-(4-aminophenyl)-benzamide. The free base is purified on a silica column (eluant: heptane/ethyl acetate: 35/65). The pure fractions are collected and concentrated under reduced pressure. The evaporation residue is diluted in 10 ml of acetone and salified with a molar solution of HCl in anhydrous ether, as described previously. 0.35 g (62%) of a yellow powder is obtained. Melting point: 199–200° C.

NMR $^1$H (400 MHz, DMSO, δ): 11.11 (s, 1H, NH$^+$); 10.29 (s, 1H, NH$^+$); 10.17 (s, 1H, NH$^+$); 9.71 (s, 1H, CONH); 8.61 (wide s, 1H, OH); 8.14 (m, 2H, thiophene); 7.79 (s, 1H, Ph-N); 7.53 (m, 1H, Ph-N); 7.48 (d, 1H, —CH═CH—, J=14.7 Hz); 7.37 (m, 4H, Ph-tBu+OH+Ph-N); 7.05 (m, 1H, thiophene); 6.68 (d, 1H, —CH═CH—); 1.41 (s, 18H, 2×tBu). IR: $v_{OH}$: 3624 cm$^{-1}$, 3415 cm$^{-1}$; $v_{C═O}$ (amide): 1656 cm$^{-1}$; $v_{C═C}$: 1616 cm$^{-1}$; $v_{C═N}$ (amidine): 1587 cm$^{-1}$.

Example 19

N-[3-[{3-(3,5-bis-(1,1-dimethylethyl)-4-hydroxyphenyl)-1-oxo-2-propenyl}-amino]-4-hydroxyphenyl]-2-thiophenecarboximidamide hydrochloride: 19

19.1) 3-[(3,5-bis-(1,1-dimethylethyl)-4-hydroxyphenyl]-N-(2-hydroxy-5-nitrophenyl)-2-propenamide:

The experimental protocol used is the same as that described for intermediate 18.1, with 2-amino-4-nitrophenol replacing the 4-amino-2-nitrophenol. A light yellow powder is obtained with a yield of 25%. Melting point: 256–257° C.

NMR $^1$H (400 MHz, DMSO, δ): 11.79 (wide s, 1H, OH); 9.59 (s, 1H, NH); 9.21 (wide s, 1H, Ph-NO$_2$); 7.90 (badly resolved dd, 1H, Ph-NO$_2$, J=8.1 Hz); 7.52 (d, 1H, —CH═CH—, J=15.5 Hz); 7.47 (s, 1H, OH); 7.42 (s, 2H, Ph-OH); 7.15 (d, 1H, —CH═CH—); 7.04 (d, 1H, Ph-NO$_2$); 1.42 (s, 18H, 2×tBu).

19.2) 3-[(3,5-bis-(1,1-dimethylethyl)-4-hydroxyphenyl]-N-(2-hydroxy-5-aminophenyl)-2-propenamide:

The experimental protocol used is the same as that described for intermediate 18.2, with 3-[(3,5-bis-(1,1-dimethylethyl)-4-hydroxyphenyl]-N-(2-hydroxy-5-nitrophenyl)-2-propenamide replacing the 3-[(3,5-bis-(1,1-dimethylethyl)-4-hydroxyphenyl]-N-(4-hydroxy-3-nitrophenyl)-2-propenamide. A yellow powder is obtained with a yield of 74%. The product is used without additional purification in the following stage.

19.3) N-[5-[{3-(3,5-bis-(1,1-dimethylethyl)-4-hydroxyphenyl)-1-oxo-2-propenyl}-amino]-2-hydroxyphenyl]-2-thiophenecarboximidamide hydrochloride: 19

The experimental protocol used is the same as that described for compound 1, with 3-[(3,5-bis-(1,1-dimethylethyl)-4-hydroxyphenyl]-N-(2-hydroxy-5-aminophenyl)-2-propenamide replacing the 3,5-bis-(1,1-dimethylethyl)-4-hydroxy-N-(4-aminophenyl)-benzamide. After salification with a molar solution of HCl in anhydrous diethyl ether, a yellow powder is obtained with a yield of 54%. Melting point: 256–257° C.

NMR $^1$H (400 MHz, DMSO d6, δ): 11.32 (s, 1H, NH$^+$); 10.67 (s, 1H, NH$^+$); 9.69 (s, 1H, NH$^+$); 9.55 (s, 1H, CONH); 8.70 (wide s, 1H, OH); 8.19 (m, 2H, thiophene); 7.48 (d, 1H, —CH═CH—, J=15.5 Hz); 7.40 (s, 2H, Ph-tBu); 7.37 (m, 2H, Ph-N); 7.34 (s, 1H, OH); 7.13 (d, 1H, —CH═CH—); 7.10 (m, 1H, Ph-N); 6.99 (m, 1H, thiophene); 1.41 (s, 18H, 2×tBu). IR: $v_{OH}$: 3623 cm$^{-1}$, 3410 cm$^{-1}$; $v_{C═O}$ (amide): 1652 cm$^{-1}$; $v_{C═C}$: 1616 cm$^{-1}$; $v_{C═N}$ (amidine): 1587 cm$^{-1}$.

Example 20

N-{4-[4-[3,4,5-trihydroxybenzoyl]-1-piperazinyl]phenyl}-2-thiophenecarboximidamide hydrochloride: 20

20.1) 5-{[4-(4-nitrophenyl)-1-piperazinyl]carbonyl}-benzene-1,2,3-triol:

The experimental protocol is the same as that described for intermediate 8.1, with 1-(4-nitrophenyl)piperazine replacing the 4-nitrophenetylamine. A yellow powder still containing traces of impurities is obtained with a yield of 43%.

NMR $^1$H (100 MHz, DMSO, δ): 9.17 (wide s, 2H, 2×—OH); 8.55 (wide s, 1H, —OH); 7.57 (m, 4H, Ph-NO$_2$); 6.40 (s, 2H, Ph-OH); 3.59 (badly resolved m, 8H, piperazine).

20.2) 5-{[4-(4-aminophenyl)-1-piperazinyl]carbonyl}-benzene-1,2,3-triol:

The experimental protocol used is the same as that described for intermediate 2.2, with 5-{[4-(4-nitrophenyl)-1-piperazinyl]carbonyl}-benzene-1,2,3-triol replacing the 3,5-bis-(1,1-dimethylethyl)-4-hydroxy-N-[(4-nitrophenyl)methyl]-benzamide. A beige powder is obtained with a yield of 61%. This is used directly in the following stage without additional purification.

NMR $^1$H (100 MHz, DMSO, δ): 9.12 (wide s, 2H, 2×—OH); 8.55 (wide s, 1H, —OH); 6.61 (m, 4H, Ph-NH$_2$); 6.34 (s, 2H, Ph-OH); 3.59 (m, 4H, piperazine); 2.89 (m, 4H, piperazine).

20.3) N-{4-[4-[3,4,5-trihydroxybenzoyl]-1-piperazinyl]phenyl}-2-thiophenecarboximidamide hydrochloride: 20

The experimental protocol used is the same as that described for compound 1, with 5-{[4-(4-aminophenyl)-1-piperazinyl]carbonyl}-benzene-1,2,3-triol replacing the 3,5-bis-(1,1-dimethylethyl)-4-hydroxy-N-(4-aminophenyl)-benzamide. After treatment with a molar solution of HCl in anhydrous diethyl ether, a brown powder is obtained with a yield of 25%. Melting point: 198–205° C.

NMR $^1$H (400 MHz, DMSO d6, δ): 11.38 (s, 1H, NH$^+$); 9.75 (s, 1H, NH$^+$); 9.00 (wide s, 1H, OH); 8.75 (s, 1H, NH$^+$); 8.15 (m, 2H, thiophene); 7.39 (m, 1H, thiophene); 7.22 (m, 4H, Ph-N); 6.40 (s, 2H, Ph); 5.11 (wide s, 2H, 2×OH); 3.65 (m, 4H, piperazine); 3.29 (m, 4H, piperazine). IR: $v_{OH}$: 3399 cm$^{-1}$; $v_{C=O}$ (amide): 1696 cm$^{-1}$; $v_{C=N}$ (amidine): 1588 cm$^{-1}$.

Example 21

N-[3,5-bis-(1,1-dimethylethyl)-4-hydroxyphenyl]-N'-{{4-[(2-thienyl(imino)methyl)amino]phenyl}carbonylamino}-urea hydrochloride: 21

21.1) N-[3,5-bis-(1,1-dimethylethyl)-4-hydroxyphenyl]-N'-[(4-nitrophenyl)-carbonylamino]-urea:

0.22 g (0.73 mmole) of triphosgene at 20° C. is dissolved in a 50 ml three-necked flask equipped with an addition funnel, under an argon atmosphere. Over one hour, a solution of 0.44 g (2 mmoles) of 4-amino-2,6-bis-(1,1-dimethylethyl)-phenol (intermediate 17.1) and 0.38 ml (2.2 mmoles) of diisopropylethylamine in 7 ml of anhydrous dichloromethane is added dropwise to this mixture. Five minutes after the end of this addition, a solution of 0.36 g (2 mmoles) of 4-nitrobenzoyl-hydrazide and 0.38 ml (2.2 mmoles) of diisopropylethylamine in 4 ml of anhydrous DMF is added in a single portion. After agitation for four hours at 20° C., the reaction medium is concentrated to dryness under reduced pressure. The evaporation residue is diluted in 40 ml of ethyl acetate and the organic solution is washed successively with 3 times 20 ml of water and 20 ml of a saturated solution of sodium chloride. After drying over sodium sulphate, the organic solution is filtered and the filtrate concentrated to dryness under reduced pressure. The residue obtained is suspended in heptane, agitated and filtered to produce a yellow powder with a yield of 86%. Melting point: 163–164° C.

NMR $^1$H (400 MHz, DMSO d6, δ): 10.65 (wide s, 1H, NH amide); 8.72 (s, 1H, NH-Ph); 8.38 (m, 4H, Ph-NO$_2$); 8.20 (s, 1H, CO—NH—NH); 7.36 (s, 2H, Ph-OH); 6.78 (s, 1H, OH); 1.50 (s, 18H, 2×tBu).

21.2) N-[(4-aminophenyl)carbonylamino]-N'-[3,5-bis-(1,1-dimethylethyl)-4-hydroxyphenyl]-urea:

In a 250 ml Parr flask, 0.72 g (1.68 mmoles) of N-[3,5-bis-(1,1-dimethylethyl)-4-hydroxyphenyl]-N'-[(4-nitrophenyl)carbonylamino]-urea is dissolved in 30 ml of absolute ethanol in the presence of 10% Pd/C. The mixture is agitated under 20 PSI of hydrogen, at 30° C., for two hours. After filtration on celite, the filtrate is concentrated under vacuum. The evaporation residue is suspended in diethyl ether (20 ml), agitated and filtered to produce a pale yellow powder with a yield of 75%. Melting point: 245–246° C.

NMR $^1$H (100 MHz, DMSO d6, δ): 9.84 (wide s, 1H, NH amide); 8.56 (s, 1H, NH-Ph); 7.85 (m, 2H, Ph-NH$_2$); 7.74 (s, 1H, CO—NH—NH); 7.38 (s, 2H, Ph-OH); 6.78 (s, 1H, OH); 6.60 (m, 2H, Ph-NH$_2$); 5.80 (wide s, 2H, NH$_2$); 1.50 (s, 18H, 2×tBu).

21.3) N-[3,5-bis-(1,1-dimethylethyl)-4-hydroxyphenyl]-N'-{{4-[(2-thienyl(imino)methyl)amino]phenyl}carbonylamino}-urea hydrochloride: 21

The experimental protocol used is the same as that described for compound 1, with N-[(4-aminophenyl)carbonylamino]-N'-[3,5-bis-(1,1-dimethylethyl)-4-hydroxyphenyl]-urea replacing the 3,5-bis-(1,1-dimethylethyl)-4-hydroxy-N-(4-aminophenyl)-benzamide. The free base is purified on a silica column (eluant: heptane/ethyl acetate: 1/1). The pure fractions are collected and concentrated under reduced pressure. The evaporation residue is diluted in 15 ml of acetone and salified with a molar solution of HCl in anhydrous ether, as described previously. 0.40 g (58%) of a yellow powder is obtained. Melting point: 254–255° C.

NMR $^1$H (400 MHz, DMSO, δ): 11.68 (wide s, 1H, NH$^+$); 10.32 (s, 1H, NH amide); 9.94 (wide s, 1H, NH$^+$); 9.13 (wide s, 1H, NH$^+$); 8.68 (s, 1H, NH—CO); 8.18 (m, 2H, thiophene); 8.07 (m, 3H, CO—NH—NH+Ph-NH); 7.58 (m, 2H, Ph-NH); 7.39 (m, 1H, thiophene); 7.22 (s, 2H, Ph-OH); 6.60 (s, 1H, OH); 1.36 (s, 18H, 2×tBu). IR: $v_{OH}$: 3627 cm$^{-1}$; $v_{C=O}$ (amide), $v_{C=O}$ (urea): 1654 cm$^{-1}$, 1602 cm$^{-1}$; $v_{C=N}$ (amidine): 1559 cm$^{-1}$.

Example 22

N-[3,5-bis-(1,1-dimethylethyl)-4-hydroxyphenyl]-N'-{{4-[(2-thienyl(imino)methyl)amino]phenyl}methyl}-thiourea hydrochloride: 22

22.1) N-[3,5-bis-(1,1-dimethylethyl)-4-hydroxyphenyl]-N'-[(4-nitrophenyl)methyl]-thiourea:

Compound 22.1 is obtained by the action of Lawesson's reagent on intermediate 17.4 according to an experimental protocol described in the literature (*J. Med. Chem.* (1995), 38 (18), 3558–3565). A light yellow powder is obtained with a yield of 80%. Melting point: 218–220° C.

NMR $^1$H (100 MHz, CDCl$_3$, δ): 7.85 (m, 4H, Ph-NO$_2$); 7.70 (s, 1H, NH-Ph); 7.05 (s, 2H, Ph-OH); 6.21 (m, 1H, NH—CH$_2$); 5.40 (s, 1H, OH); 5.00 (d, 2H, CH$_2$, J=6.5 Hz); 1.41 (s, 18H, 2×tBu).

2.2) N-[(4-aminophenyl)methyl]-N'-[3,5-bis-(1,1-dimethylethyl)-4-hydroxyphenyl]-thiourea:

The experimental protocol used is the same as that described for intermediate 18.2, with intermediate 22.1 replacing the 3-[(3,5-bis-(1,1-dimethylethyl)-4-hydroxyphenyl]-N-(4-hydroxy-3-nitrophenyl)-2-propenamide. A beige powder is obtained with a yield of 70%. Melting point: 167–169° C.

NMR $^1$H (100 MHz, CDCl$_3$, δ): 7.48 (wide s, 1H, NH-Ph); 6.95 (s, 2H, Ph-OH); 6.81 (m, 4H, Ph-NH$_2$); 5.98 (m, 1H, NH—CH$_2$); 5.28 (s, 1H, OH); 4.69 (d, 2H, CH$_2$, J=5.5 Hz); 3.62 (wide s, 2H, NH$_2$); 1.40 (s, 18H, 2×tBu).

22.3) N-[3,5-bis-(1,1-dimethylethyl)-4-hydroxyphenyl]-N'-{4-[(2-thienyl(imino)methyl)amino]phenyl}methyl}-thiourea hydrochloride: 22

The experimental protocol used is the same as that described for intermediate 17.6, with intermediate 22.2 replacing the N-[(4-aminophenyl)methyl]-N'-[3,5-bis-(1,1-dimethylethyl)-4-hydroxyphenyl]-urea. A pale yellow powder is obtained with a yield of 15%. Melting point: 203–205° C.

NMR $^1$H (400 MHz, DMSO d6, δ): 11.52 (wide s, 1H, NH$^+$); 9.86 (wide s, 1H, NH$^+$); 8.98 (wide s, 1H, NH$^+$); 8.39 (s, 1H, NH-Ph); 8.16 (m, 2H, thiophene); 7.46 (m, 6H, Ph-N, thiophene, NH—CH$_2$); 7.18 (s, 2H, Ph); 6.92 (s, 1H, OH); 4.80 (wide s, 2H, CH$_2$); 1.35 (s, 18H, 2×tBu). IR: $v_{OH}$: 3630 cm$^{-1}$; $v_{C=O}$ (urea): 1649 cm$^{-1}$; $v_{C=N}$ (amidine): 1600 cm$^{-1}$.

Example 23

N-[3,5-bis-(1,1-dimethylethyl)-4-hydroxyphenyl]-N'-{2-{4-[(2-thienyl(imino)methyl)amino]phenylethyl}-urea hydrochloride: 23

23.1) N-[3,5-bis-(1,1-dimethylethyl)-4-hydroxyphenyl]-N'-[2-(4-nitrophenyl)ethyl]-urea:

The experimental protocol used is the same as that described for intermediate 21.1, with 4-nitrophenetylamine replacing the 4-nitrobenzoyl-hydrazide. A beige powder is obtained with a yield of 80%. Melting point: 185–187° C.

NMR $^1$H (100 MHz, CDCl$_3$, δ): 7.75 (m, 4H, Ph-NO$_2$); 7.00 (s, 2H, Ph-OH); 6.05 (s, 1H, OH); 5.18 (s, 1H, NH); 4.68 (m, 1H, NH—CH$_2$); 3.50 (m, 2H, NH-CH$_2$); 2.92 (m, 2H, CH$_2$); 1.40 (s, 18H, 2×tBu).

23.2) N-[2-(4-aminophenyl)ethyl]-N'-[3,5-bis-(1,1-dimethylethyl)-4-hydroxyphenyl]-urea:

The experimental protocol used is the same as that described for intermediate 21.2, with intermediate 23.1 replacing the N-[3,5-bis-(1,1-dimethylethyl)-4-hydroxyphenyl]-N'-[(4-nitrophenyl)-carbonylamino]-urea. A white powder is obtained with a yield of 56%. Melting point: 192–194° C.

NMR $^1$H (100 MHz, DMSO d6, δ): 8.25 (wide s, 1H, Ph-NH—CO); 7.22 (s, 2H, Ph-OH); 6.79 (m, 4H, Ph-NH$_2$); 6.65 (s, 1H, OH); 5.92 (m, 1H, NH—CH$_2$); 4.98 (wide s, 2H, —NH$_2$); 3.31 (m, 2H, NH—CH$_2$); 2.65 (m, 2H, CH$_2$) 1.48 (s, 18H, 2×tBu).

23.3) N-[3,5-bis-(1,1-dimethylethyl)-4-hydroxyphenyl]-N'-{2-{4-[(2-thienyl(imino)methyl)amino]phenyl}ethyl}-urea hydrochloride: 23

The experimental protocol used is the same as that described for compound 1, with intermediate 23.2 replacing the 3,5-bis-(1,1-dimethylethyl)-4-hydroxy-N-(4-aminophenyl)-benzamide. The free base is purified on a silica column (eluant: heptane/ethyl acetate: 1/1). The pure fractions are collected and concentrated under reduced pressure. The evaporation residue is diluted in 15 ml of acetone and salified with a molar solution of HCl in anhydrous ether, as described previously. Finally, 0.25 g (24%) of a pale yellow powder is obtained. Melting point: 207–210° C.

NMR $^1$H (400 MHz, DMSO d6, δ): 11.48 (wide s, 1H, NH$^+$); 9.83 (wide s, 1H, NH$^+$); 8.95 (wide s, 1H, NH$^+$); 8.50 (s, 1H, NH—CO); 8.18 (m, 2H, thiophene); 7.38 (m, 5H, Ph-NH+thiophene); 7.18 (s, 2H, Ph-OH); 6.55 (s, 1H, OH); 6.21 (m, 1H, CO—NH—CH$_2$); 3.35 (m, 2H, NH—CH$_2$); 2.78 (m, 2H, CH$_2$); 1.36 (s, 18H, 2×tBu). IR: $v_{OH}$: 3631 cm$^{-1}$; $v_{C=O}$ (urea): 1654 cm$^{-1}$, 1600 cm$^{-1}$; $v_{C=N}$ (amidine): 1560 cm$^{-1}$.

Example 24

N-(4-{4-[(3,4-dihydro-6-methoxy-2,5,7,8-tetramethyl-2H-1-benzopyran-2-yl)carbonyl]-1-piperazinyl}phenyl)-2-thiophenecarboximidamide hydrochloride: 24

24.1) 1-{[3,4-dihydro-6-methoxy-2,5,7,8-tetramethyl-2H-1-benzopyran-2-yl]carbonyl}-4-(4-nitrophenyl)piperazine:

The experimental protocol is identical to that described for intermediate 13.1, with (±)-3,4-dihydro-6-methoxy-2,5,7,8-tetramethyl-2H-1-benzopyran-2-carboxylique acid (prepared according to CHIMIA (1991), 45 (4), 121–3) replacing the (±)-Trolox®. A yellow powder is obtained.

NMR $^1$H (100 MHz, CDCl$_3$, δ): 7.45 (m, 4H, Ph); 3.60 (s, 3H, CH$_3$O);®3.40 (m, 4H, piperazine); 3.00 (m, 4H, piperazine); 2.50–1.60 (m, 16H, Trolox®).

24.2) 1-([3,4-dihydro-6-methoxy-2,5,7,8-tetramethyl-2H-1-benzopyran-2-yl]carbonyl}-4-(4-aminophenyl)piperazine:

The experimental protocol is identical to that described for intermediate 13.2, with intermediate 24.1 replacing the 3,4-dihydro-2,5,7,8-tetramethyl-2-{4-[(4-nitrophenyl)-1-piperazinyl]-carbonyl}-2H-1-benzopyran-6-ol. An oil is obtained which is used directly in the following stage.

NMR 1H (100 MHz, CDCl$_3$, δ): 6.70 (m, 4H, Ph); 3.90 (wide d, 4H, piperazine); 3.60 (s, 3H, CH$_3$O); 3.45 (wide s, 2H, NH$_2$); 2.90 (m, 4H, piperazine); 2.60–1.60 (m, 18H, Trolox®).

24.3) N-(4-{4-[(3,4-dihydro-6-methoxy-2,5,7,8-tetramethyl-2H-1-benzopyran-2-yl)carbonyl]-1-piperazinyl}phenyl)-2-thiophenecarboximidamide hydrochloride: 24

The experimental protocol is the same as that described for compound 13, with intermediate 24.2 replacing the 3,4-dihydro-2,5,7,8-tetramethyl-2-{4-[(4-aminophenyl)-1-piperazinyl]-carbonyl}-2H-1-benzopyran-6-ol. A pale yellow powder is obtained. Melting point: 190–195° C.

NMR $^1$H (400 MHz, DMSO, δ): 11.35 (wide s, 1H, NH$^+$); 9.70 (wide s, 1H, NH$^+$); 8.70 (wide s, 1H, NH$^+$); 8.15 (wide s, 2H, thiophene); 7.35 (wide s, 1H, thiophene); 7.17 (m, 4H, Ph); 3.90 (wide d, 4H, piperazine); 3.50 (s, 3H, CH$_3$O); 3.15 (m, 4H, piperazine); 2.55–1.55 (m, 16H, Trolox®). IR: $v_{C=O}$ (amide): 1642 cm$^{-1}$; $v_{C=N}$ (amidine): 1618 cm$^{-1}$.

Example 25

N-[4-{4-[(3,4-dihydro-6-hydroxy-2,5,7,8-tetramethyl-2H-1-benzopyran-2-yl)carbonyl]-1H-1,4-diazepin-1-yl}phenyl]-2-thiophenecarboximidamide hydrochloride: 25

25.1) hexahydro-4-(4-nitrophenyl)-1H-1,4-diazepine:

3.37 g (24.4 mmoles) of potassium carbonate and 1.89 g (13.4 mmoles) of 4-nitrofluorobenzene are added to a solution of 2.44 g (12.2 mmoles) of (1,1-dimethyl) ethyl hexahydro-1H-1,4-diazepine-1-carboxylate in 50 ml of DMF. The reaction medium is heated at 100° C. for 16 hours. After cooling down, 25 ml of ethyl acetate and 50 ml of water are added. The organic solution is decanted and the aqueous phase extracted with 3 times 50 ml of ethyl acetate. The organic phases are collected together and washed with 50 ml of brine, dried over sodium sulphate, filtered and concentrated under vacuum. 3.7 g of a bright yellow solid is obtained with a yield of 95%. This solid is then dissolved in 100 ml of a mixture of solvents (dichloromethane/ethyl acetate 1:1) to which 20 ml of a 6N aqueous solution of hydrochloric acid is added dropwise at 0° C. After vigorous agitation at 20° C. for 1 hour, the reaction medium is decanted. The aqueous phase is basified to pH=11 with 4N soda and extracted with 3 times 50 ml of dichloromethane. The organic phases are collected, washed with 50 ml of water followed by 50 ml of brine, dried over sodium sulphate and finally filtered and concentrated under vacuum. 1.78 g of a bright yellow powder is obtained with a yield of 66%. The product is used directly in the following stage without additional purification.

NMR $^1$H (100 MHz, CDCl$_3$, δ): 8.10 (m, 2H, Ph); 6.65 (m, 2H, Ph); 3.70 (q, 4H, CH$_2$N, J=5.2 Hz); 3.10 (t, 2H, CH$_2$N); 2.85 (t, 2H, CH$_2$N); 1.95 (q, 2H, C—CH$_2$—C); 1.65 (wide s, 1H NH).

25.2) 1-[(3,4-dihydro-6-hydroxy-2,5,7,8-tetramethyl-2H-1-benzopyran-2-yl)carbonyl]hexahydro-4-(4-nitrophenyl)-1H-1,4-diazepine:

In a 50 ml flask, 0.71 g (4.4 mmoles) of 1,1'-carbonyldiimidazole is added to a solution of 1.07 g (4.3 mmoles) of (±)-Trolox® in 8 ml of anhydrous THF. After agitation for one hour at 20° C., a solution of 0.95 g (4.3 mmoles) of intermediate 25.1 in 4 ml of DMF is added dropwise. The reaction medium is agitated for 16 hours at 20° C. After evaporation of the solvents under vacuum, the residue is taken up in 30 ml of a mixture of solvents (dichloromethane/water 1:2). After decanting, the organic phase is washed with 2 times 20 ml of water, dried over sodium sulphate and concentrated under vacuum. A pale yellow powder is obtained with a gross yield of 97%. The product is used directly in the following stage without additional purification.

NMR $^1$H (100 MHz, CDCl$_3$, δ): 8.10 (m, 2H, Ph); 6.60 (m, 2H, Ph); 4.40 (wide s, 1H, OH); 3.50 (m, 8H, CH$_2$N); 2.50–1.50 (m, 18H, Trolox®+CH$_2$).

25.3) 1-(4-aminophenyl)-4-[(3,4-dihydro-6-hydroxy-2,5,7,8-tetramethyl-2H-1-benzopyran-2-yl)carbonyl]hexahydro-1H-1,4-diazepine:

The experimental protocol used is the same as that described for intermediate 13.2, with intermediate 25.2 replacing the 3,4-dihydro-2,5,7,8-tetramethyl-2-{4-[(4-nitrophenyl)-1-piperazinyl]-carbonyl}-2H-1-benzopyran-6-ol. The product of the reaction is purified on a silica gel column (eluant: ethyl acetate/petroleum ether 3:2). An oil is obtained with a yield of 57%.

25.4) N-[4-{4-[(3,4-dihydro-6-hydroxy-2,5,7,8-tetramethyl-2H-1-benzopyran-2-yl)carbonyl]-1H-1,4-diazepin-1-ylphenyl]-2-thiophenecarboximidamide hydrochloride:

A mixture of 0.52 g (1.22 mmole) of intermediate 25.3 and 0.35 g (1.22 mmole) of S-methyl-2-thiophene thiocarboximide hydriodide in 4 ml of isopropanol is heated at 50° C. for 40 hours. The reaction medium is then filtered and the solid obtained is taken up in 4 ml of a saturated aqueous solution of sodium carbonate and 4 ml of ethyl acetate. The mixture is heated at 50° C. for 30 minutes, then decanted. The organic phase is washed twice with 10 ml of water followed by 10 ml of brine. The organic phases are collected, dried over sodium sulphate, filtered and concentrated under reduced pressure. The solid obtained is purified on a silica gel column (eluant: ethyl acetate/petroleum ether 5:1). 0.5 g of product is obtained with a yield of 77%. 0.15 g (0.29 mmole) of this product is then dissolved in 2 ml of acetone. 0.84 ml (0.84 mmole) of a 1N hydrochloric acid solution in anhydrous ethyl ether is added dropwise. The whole is agitated at ambient temperature for 30 minutes. A yellow precipitate forms which is filtered. The precipitate is triturated and washed successively with 3 times 5 ml of ethyl ether and 5 ml of acetone. The dark yellow powder is dried under vacuum at 70° C. for 48 hours. The yield obtained is 80%. Melting point: 180–185° C.

NMR $^1$H (400 MHz, DMSO, δ): 11.15 (wide s, 1H, NH$^+$); 9.60 (wide s, 1H, NH$^+$); 8.55 (wide s, 1H, NH$^+$); 8.10 (wide s, 2H, thiophene); 7.35 (wide s, 1H, thiophene); 7.02 (m, 4H, Ph); 4.80 (wide s, 1H, OH); 3.70 (m, 8H, CH$_2$N); 2.50–1.40 (m, 18H, Trolox®+CH$_2$). IR: $\nu_{OH}$: 3412 cm$^{-1}$; $\nu_{C=O}$ (amide): 1613 cm$^{-1}$; $\nu_{C=N}$ (amidine): 1613 cm$^{-1}$.

Example 26

(R)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide hydrochloride: 26

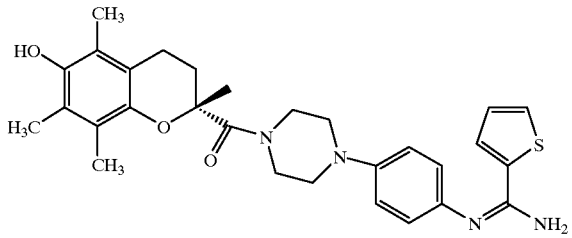

26.1) (R)-3,4-dihydro-2,5,7,8-tetramethyl-2-{4-[(4-nitrophenyl)-1-piperazinyl]-carbonyl}-2H-1-benzopyran-6-ol:

The experimental protocol used is the same as that described for compound 13. 1, with (R)-Trolox® replacing the (±)Trolox®. A bright yellow powder is obtained with a yield of 98%. Melting point: 102–105° C.

26.2) (R)-3,4-dihydro-2,5,7,8-tetramethyl-2-{4-[(4-aminophenyl)-1-piperazinyl]-carbonyl}-2H-1-benzopyran-6-ol:

The experimental protocol used is the same as that described for intermediate 2.2, with intermediate 26.1 replacing the 3,5-bis-(1,1-dimethylethyl)-4-hydroxy-N-[(4-nitrophenyl)methyl]-benzamide. A pink powder is obtained with a yield of 75%. The product is used as it is in the following stage. Melting point: 103–105° C.

26.3) (R)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide hydrochloride: 26

The experimental protocol used is the same as that described for compound 13, with intermediate 26.2 replacing the 3,4-dihydro-2,5,7,8-tetramethyl-2-{4-[(4-aminophenyl)-1-piperazinyl)-carbonyl}-2H-1-benzopyran-6-ol. The product is obtained in the form of a pale yellow powder which hydrates in air. Melting point: 195–197° C.

The NMR and IR analyses are identical to compound 13.

$[\alpha]_D^{20} = -43.5°$ (c = 0.11; DMSO)

Example 27

(S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide dihydrochloride: 27

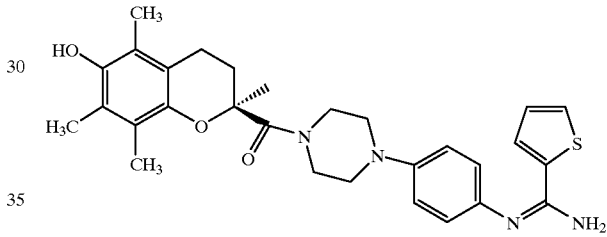

27.1) (S)-3,4-dihydro-2,5,7,8-tetramethyl-2-(4-[(4-nitrophenyl)-1-piperazinyl]-carbonyl}-2H-1-benzopyran-6-ol:

The experimental protocol used is the same as that described for compound 13.1, with (S)-Trolox® replacing the (±)Trolox®. A yellow powder is obtained with a yield of 73%. Melting point: 110–111° C.

27.2) (S)-3,4-dihydro-2,5,7,8-tetramethyl-2-{4-[(4-aminophenyl)-1-piperazinyl)-carbonyl}-2H-1-benzopyran-6-ol:

The experimental protocol used is the same as that described for intermediate 2.2, with intermediate 27.1 replacing the 3,5-bis-(1,1-dimethylethyl)-4-hydroxy-N-[(4-nitrophenyl)methyl]-benzamide. After purification on a silica gel column (heptane/ethyl acetate: 2/8), collection and evaporation under vacuum of the pure fractions, a beige powder is obtained with a yield of 54%. Melting point: 109–111° C.

27.3) (S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide dihydrochloride: 27

The experimental protocol used is the same as that described for compound 13, with intermediate 27.2 replacing the 3,4-dihydro-2,5,7,8-tetramethyl-2-{4-[(4-aminophenyl)-1-piperazinyl)-carbonyl}-2H-1-benzopyran-6-ol. The product is obtained in the form of a pale yellow powder which hydrates in air. Melting point: 210.6–211.8° C.

The NMR and IR analyses are identical to compound 13.

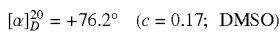
$[\alpha]_D^{20} = +76.2°$ (c = 0.17; DMSO)

Alternatively, compound 27 can be prepared according to the following protocol:

27.4) methyl 2-thiophene carboximidate:

10.91 g (0.1 mole) of 2-thiophene carbonitrile, 100 ml of anhydrous ethyl ether and 4.5 ml (0.11 mole) of methanol are introduced into a 250 ml erlen meyer flask purged with argon. The solution is cooled down to 0° C. using an ice bath and saturated with a stream of anhydrous gaseous HCl for 45 minutes. The reaction medium is agitated for an additional hour at 0° C. and overnight at 20° C. The precipitate formed is filtered out, washed with ethyl ether and dried. The hydrochloride obtained is partitioned into a mixture of 100 ml of water and 150 ml of ethyl ether. The medium is neutralized by adding 8.4 g (0.1 mole) of dry NaHCO₃. After decanting and separation, the organic phase is washed successively with 2×30 ml of water and 30 ml of brine. After drying over magnesium sulphate, the organic solution is filtered and concentrated under vacuum. A colourless oil is obtained with a yield of 66%.

NMR $^1$H (400 MHz, CDCl₃, δ): 7.58 (wide s, 1H, =N—H); 7.42 (m, 1H, thiophene); 7.37 (m, 1H, thiophene); 7.01 (m, 1H, thiophene); 3.86 (s, 3H, OCH₃). IR: $v_{C=N}$ (carboximidate): 1630 cm$^{-1}$.

27.5) (S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide dihydrochloride: 27

In a 150 ml erlen meyer flask, under a stream of argon, 8.2 g (20 mmoles) of (S)-3,4-dihydro-2,5,7,8-tetramethyl-2-{4-[(4-aminophenyl)-1-piperazinyl]-carbonyl}-2H-1-benzopyran-6-ol (obtained as intermediate 13.2 but from (S)-Trolox®), is dissolved in 60 ml of methanol and 4.2 g (30 mmoles) of methyl 2-thiophene carboximidate is added. The reaction medium is heated for 18 hours under reflux. The methanol is evaporated under vacuum and the oily brown residue is purified on a silica gel column (eluant: dichloromethane/ethanol: 95/5). The pure fractions are collected and concentrated under vacuum to produce a brown oil with a yield of 68%. This oil is taken up in 22 ml of an ethanolic solution of HCl (1.3N) and diluted with 180 ml of anhydrous acetone. The reaction medium is agitated for 1 hour at 0° C. The precipitate formed is filtered and washed successively with acetone and ethyl ether. After drying, the dihydrochloride is obtained in the form of a pale yellow powder with a yield of 53%.

Example 28

3,5-bis-(1,1-dimethylethyl)-4-hydroxy-N-{2-[3-[(2-thienyl(imino)methyl)amino]phenyl]ethyl}-benzamide hydrochloride: 28

28.1) 3,5-bis-(1,1-dimethylethyl)-4-hydroxy-N-[2-(3-nitrophenyl)ethyl]-benzamide:

The experimental protocol used is the same as that described for intermediate 5.1, with 3-nitrophenetylamine (J. Med. Chem. (1968), 11 (1), 21–26) replacing the 4-nitrophenetylamine. A white powder is obtained with a yield of 50%. Melting point: 195–197° C.

NMR $^1$H (100 MHz, CDCl₃, δ): 7.86 (m, 4H, Ph-NO₂); 7.50 (s, 2H, Ph); 6.10 (m, 1H, NHCO); 5.54 (s, 1H, OH); 3.75 (m, 2H, CH₂—NHCO); 3.08 (m, 2H, CH₂-Ph-NO₂); 1.42 (s, 18H, 2xtBu).

28.2) 3,5-bis-(1,1-dimethylethyl)-4-hydroxy-N-[2-(3-aminophenyl)ethyl]-benzamide:

The experimental protocol used is the same as that described for intermediate 5.2, with intermediate 28.1 replacing the 3,5-bis-(1,1-dimethylethyl)-4-hydroxy-N-[2-(4-nitrophenyl)ethyl]-benzamide. A white powder is obtained (yield of 40%) which is sufficiently pure to be used directly in the following stage.

28.3) 3,5-bis-(1,1-dimethylethyl)-4-hydroxy-N-{2-[3-[(2-thienyl-(imino)methyl)-amino]phenyl]ethyl}-benzamide hydrochloride: 28

The experimental protocol used is the same as that described for intermediate 1.3, with intermediate 28.2 replacing the 3,5-bis-(1,1-dimethylethyl)-4-hydroxy-N-(4-aminophenyl)-benzamide. A pale yellow powder is obtained with a yield of 35%. Melting point: 205–207° C.

NMR $^1$H (400 MHz, DMSO d6, δ): 11.59 (wide s, 1H, NH⁺); 9.89 (s, 1H, NH⁺); 8.95 (s, 1H, NH⁺); 8.46 (s, 1H, CONH); 8.17 (m, 2H, thiophene); 7.54 (s, 2H, Ph-OH); 7.39 (m, 6H, thiophene, Ph-NH, OH); 3.51 (m, 2H, CH₂—NHCO); 2.89 (m, 2H, CH₂-Ph-NH); 1.38 (s, 18H, 2xtBu). IR: $v_{OH}$: 3624 cm$^{-1}$; $v_{C=O}$ (amide): 1631 cm$^{-1}$; $v_{C=N}$ (amidine): 1577 cm$^{-1}$.

Example 29

N-{4-(4-[2-(3,5-bis-(1,1-dimethylethyl)-4-hydroxyphenyl)-1-oxo-ethyl]-1-piperazinyl)phenyl}-2-thiophene-carboximidamide hydrochloride: 29

The experimental protocol used is the same as that described for the compound 9, with 3,5-di-tert-butyl-4-hydroxyphenylacetic acid replacing the 3,5-di-tert-butyl-4-hydroxybenzoic acid in the first stage of synthesis. Yellow powder. Melting point: 176–180° C.

NMR $^1$H (400 MHz, DMSO d6, δ): 11.30 (wide s, 1H, NH⁺); 9.70 (wide s, 1H, NH⁺); 8.65 (wide s, 1H, NH⁺); 8.10 (wide s, 2H, thiophene); 7.35 (wide s, 1H, thiophene); 7.12 (m, 4H, Ph-N); 6.95 (s, 2H, Ph-OH); 6.80 (wide s, 1H, OH); 3.60 (wide s, 6H, piperazine, CH₂CO); 3.10 (m, 4H, piperazine); 1.35 (s, 18H, 2× tBu). IR: $v_{OH}$: 3620 cm$^{-1}$; $v_{C=O}$ (ester): 1638 cm$^{-1}$: $v_{C=N}$ (amidine): 1612 cm$^{-1}$.

Example 30

2-{4-[(2-thienyl(imino)methyl)amino]phenyl}ethyl 3,5-bis-(1,1-dimethylethyl)-4-hydroxy-benzoate hydrochloride: 30

30.1) 2-(4-nitrophenyl)ethyl 3,5-bis-(1,1-dimethylethyl)-4-hydroxybenzoate:

In a 250 ml flask containing 80 ml of THF, under an argon atmosphere, 2.45 g (9.8 mmoles) of 3,5-di-tert-butyl-4-hydroxybenzoic acid, 1.8 g (10.8 mmoles) of 4-nitrobenzene-ethanol and 2.2 g (10.8 mmoles) of dicyclohexylcarbodiimide are introduced successively, under agitation. The reaction medium is agitated for 15 hours at 20° C. and the precipitate which appears is filtered out. The filtrate is washed with 2×30 ml of a saturated NaCl solution, the organic phase is dried over magnesium sulphate, filtered and concentrated under vacuum. The residue is then crystallized using di-isopropyl ether. The solid is recovered by filtration and 2.4 g (62%) of white crystals are obtained after drying. Melting point: 123.5–124.5° C.

NMR $^1$H (100 MHz, CDCl₃, δ): 7.85 (m, 4H, Ph-NO₂); 7.80 (s, 2H, Ph-OH); 5.70 (s, 1H, OH); 4.50 (m, 2H, O—CH₂); 3.20 (m, 2H, CH₂); 1.40 (s, 18H, 2× tBu).

30.2) 2-(4-aminophenyl)ethyl 3,5-bis-(1,1-dimethylethyl)-4-hydroxy-benzoate:

The experimental protocol is the same as that described for intermediate 2.2, with intermediate 30.1 replacing the 3,5-bis-(1,1-dimethylethyl)-4-hydroxy-N-[(4-nitrophenyl)-methyl]-benzamide. A white powder is obtained with a yield of 50%. Melting point: 135–136° C.

NMR $^1$H (400 MHz, DMSO d6, δ): 7.75 (s, 2H, Ph-OH); 6.70 (m, 4H, Ph-N); 4.90 (wide s, 1H, OH); 4.25 (m, 2H, O—CH$_2$); 3.30 (wide s, 2H, NH$_2$); 2.80 (m, 2H, CH$_2$); 1.40 (s, 18H, 2×tBu).

30.3) 2-{4-[(2-thienyl(imino)methyl)amino]phenyl}ethyl 3,5-bis-(1,1-dimethylethyl)-4-hydroxy-benzoate hydrochloride: 30

The experimental protocol is the same as that described for intermediate 1.3, with intermediate 30.2 replacing the 3,5-bis-(1,1-dimethylethyl)-4-hydroxy-N-(4-aminophenyl)-benzamide. A white solid is obtained with a yield of 26%. Melting point: 145–150° C.

NMR $^1$H (400 MHz, DMSO d6, δ): 11.50 (wide s, 1H, NH$^+$); 9.80 (wide s, 1H, NH$^+$); 8.90 (wide s, 1H, NH$^+$); 8.20 (wide s, 2H, thiophene); 7.85 (s, 1H, OH); 7.75 (s, 2H, Ph-OH); 7.47 (m, 5H, Ph-N, thiophene); 4.41 (m, 2H, O—CH$_2$); 3.08 (m, 2H, CH$_2$);1.40 (s, 18H, 2×tBu). IR: $v_{C=O}$ (ester): 1700 cm$^{-1}$; $v_{C=N}$ (amidine): 1592 cm$^{-1}$.

Example 31

2-{3-[(2-thienyl(imino)methyl)amino]phenyl}ethyl 3,5-bis-(1,1-dimethylethyl)-4-hydroxy-benzoate hydrochloride: 31

The experimental protocol used is the same as that described for the compound 30, with 3-nitrobenzene-ethanol replacing the 4-nitrobenzene-ethanol in the first stage of synthesis. Pale yellow powder. Melting point: 145–148° C.

NMR $^1$H (400 MHz, DMSO d6, δ): 11.50 (wide s, 1H, NH$^+$); 9.82 (wide s, 1H, NH$^+$); 8.99 (wide s, 1H, NH$^+$); 8.15 (m, 2H, thiophene); 7.81 (s, 1H, OH); 7.75 (s, 2H, Ph-OH); 7.41 (m, 5H, Ph-N, thiophene); 4.41 (m, 2H, O—CH$_2$); 3.08 (m, 2H, CH$_2$); 1.38 (s, 18H, 2×tBu). IR: $v_{OH}$: 3620 cm$^{-1}$; $v_{C=O}$ (ester): 1707 cm$^{-1}$; $v_{C=N}$ (amidine): 1654 cm$^{-1}$.

Example 32

2-{2-[(2-thienyl(imino)methyl)amino]phenyl}ethyl 3,5-bis-(1,1-dimethylethyl)-4-hydroxy-benzoate hydrochloride: 32

The experimental protocol used is the same as that described for compound 30, with 2-nitrobenzene-ethanol replacing the 4-nitrobenzene-ethanol in the first stage of synthesis. Beige powder. Melting point: 139–145° C.

NMR $^1$H (400 MHz, DMSO d6, δ): 11.50 (wide s, 1H, NH$^+$); 9.80 (wide s, 1H, NH$^+$); 8.65 (wide s, 1H, NH$^+$); 8.15 (m, 2H, thiophene); 7.80 (s, 1H, OH); 7.70 (s, 2H, Ph-OH); 7.60 (m, 1H, Ph); 7.45 (m, 3H, Ph); 7.35 (s, 1H, thiophene); 4.40 (m, 2H, O—CH$_2$); 3.00 (m, 2H, CH$_2$); 1.35 (s, 18H, 2×tBu). IR: $v_{C=O}$ (ester): 1728 cm$^{-1}$; $v_{C=N}$(amidine): 1649 cm$^{-1}$.

Pharmacological Study of the Products of the Invention

Study of the Effects on Neuronal Constitutive NO Synthase of a Rat's Cerebellum

The inhibitory activity of the products of the invention is determined by measuring their effects on the conversion by NO synthase of [$^3$H]L-arginine into [$^3$H]L-citrulline according to the modified method of Bredt and Snyder (*Proc. Natl. Acad. Sci. USA*, (1990) 87: 682–685). The cerebellums of Sprague-Dawley rats (300 g—Charles River) are rapidly removed, dissected at 4° C. and homogenized in a volume of extraction buffer (HEPES 50 mM, EDTA 1 mM, pH 7.4, pepstatin A 10 mg/ml, leupeptin 10 mg/ml). The homogenates are then centrifuged at 21000 g for 15 min at 4° C. Dosage is carried out in glass test tubes in which 100 μl of incubation buffer containing 100 mM of HEPES (pH 7.4), 2 mM of EDTA, 2.5 mM of CaCl$_2$, 2 mM of dithiotreitol, 2 mM of reduced NADPH and 10 μg/ml of calmodulin are distributed. 25 μl of a solution containing 100 nM of [$^3$H]L-arginine (Specific activity: 56.4 Ci/mmole, Amersham) and 40 μM of non-radioactive L-arginine is added. The reaction is initiated by adding 50 μl of homogenate, the final volume being 200 μl (the missing 25 μl are either water or the tested product). After 15 min, the reaction is stopped with 2 ml of stopping buffer (20 mM of HEPES, pH 5.5, 2 mM of EDTA). After placing the samples on a 1 ml column of DOWEX resin, the radioactivity is quantified by a liquid scintillation spectrometer. The compounds of examples 6, 7, 13 and 14 described above show an IC$_{50}$ lower than 3.5 μM.

Study of the Effects on Lipidic Peroxidation of the Cerebral Cortex of a Rat

The inhibitory activity of the products of the invention is determined by measuring their effects on the degree of lipidic peroxidation, determined by the concentration of malondialdehyde (MDA). The MDA produced by peroxidation of unsaturated fatty acids is a good indication of lipidic peroxidation (H Esterbauer and K H Cheeseman, *Meth. Enzymol.* (1990) 186: 407–421). Male Sprague Dawley rats of 200 to 250 g (Charles River) were sacrificed by decapitation. The cerebral cortex is removed, then homogenized using a Thomas potter in a 20 mM Tris-HCl buffer, pH=7.4. The homogenate was centrifuged twice at 50000 g for 10 minutes at 4° C. The pellet is maintained at −80° C. On the day of the experiment, the pellet is replaced in suspension at a concentration of 1 g/15 ml and centrifuged at 515 g for 10 minutes at 4° C. The supernatant is used immediately to determine the lipidic peroxidation. The homogenate of rat's cerebral cortex (500 μl) is incubated at 37° C. for 15 minutes in the presence of the compounds to be tested or of solvent (10 μl). The lipidic peroxidation reaction is initiated by adding 50 μl of FeCl$_2$ at 1 mM, EDTA at 1 mM and ascorbic acid at 4 mM. After 30 minutes of incubation at 37° C., the reaction is stopped by adding 50 μl of a solution of hydroxylated di tertio butyl toluene (BHT, 0.2%). The MDA is quantified using a colorimetric test, by reacting a chromogenic reagent (R), N-methyl-2-phenylindol (650 μl) with 200 μl of the homogenate for 1 hour at 45° C. The condensation of an MDA molecule with two molecules of reagent R produce a stable chromophore the maximum absorbence wavelength of which is equal to 586 nm. (Caldwell et al. *European J. Pharmacol.* (1995) 285, 203–206). The compounds of Examples 5, 8, 9, 10, 12, 13, 14, 16, 17, 18, 19, 20, 21, 26 and 27 described above all show an IC$_{50}$ lower than 30 μM.

What is claimed is:

1. A compound selected from the group consisting of a compound of the formula

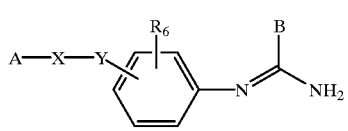

I wherein A is

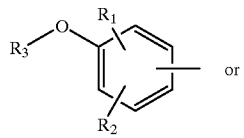

or

-continued

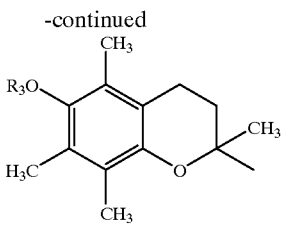

$R_1$ and $R_2$ are individually selected from the group consisting of hydrogen, halogen, —OH, alkyl of 1 to 6 carbon atoms and alkoxy of 1 to 6 carbon atoms, $R_3$ is selected from the group consisting of hydrogen, alkyl of 1 to 6 carbon atoms and —$COR_4$, $R_4$ is alkyl of 1 to 6 carbon atoms, B is selected from the group consisting of thiophene, furan, and pyrrole, X is selected from the group consisting of —$Z_1$—, —$Z_1CO$—, —CH=CH=CO—, —$Z_1NR_3$—CO—, —Z—$NR_3$—CS—, —$Z_1NR_3$—$SO_2$— and a single bond, Y is selected from the group consisting of —$Z_2$—Q—, —$NR_3$—$Z_2$—Q—, —$NR_3$—CO—$Z_2$—Q, —$NR_3$—NH—CO—$Z_2$—, —NH—NH—$Z_2$—, —$NR_3$—O—$Z_2$—, —$NR_3$—$SO_2$—$NR_3$—$Z_2$—, —$OZ_2$—Q—, —O—CO—$Z_2$—Q— and —S—$Z_3$—Q—, Q is selected from the group consisting of a single bond, —$OZ_3$—, —$SZ_2$— and —$NR_3$—$Z_3$, $Z_1$, $Z_2$ and $Z_3$ are individually selected from the group consisting of a single bond and alkylene of 1 to 6 carbon atoms, $R_6$ is hydrogen or —OH and its non-toxic, pharmaceutically acceptable salts with the proviso that it is not the compound of the formula

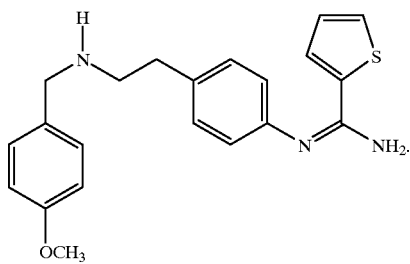

E

2. A compound of claim 1 wherein A is

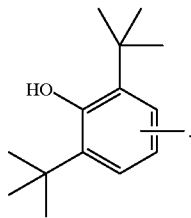

3. A compound according to claim 1 selected from the group consisting of:
3,5-bis-(1,1-dimethylethyl)-4-hydroxy-N-{4-[(2-thienyl(imino)methyl)amino]phenyl}-benzamide;
3,5-bis-(1,1-dimethylethyl)-4-hydroxy-N-{4-[[(2-thienyl(imino)methyl)amino]-phenyl]methyl}-benzamide;
4-acetoxy-3,5-dimethoxy-N-{4-[[(2-thienyl(imino)methyl)amino]phenyl]methyl}-benzamide;
3,5-dimethoxy-4-hydroxy-N-{4-[[(2-thienyl(imino)methyl)amino]phenyl]methyl}-benzamide;
3,5-bis-(1,1-dimethylethyl)-4-hydroxy-N-{4-[2-[(2-thienyl(imino)methyl)amino]phenyl]ethyl}-benzamide;
4-acetoxy-3,5-dimethoxy-N-{4-[2-[(2-thienyl(imino)methyl)-amino]phenyl]ethyl}-benzamide;
3,5-dimethoxy-4-hydroxy-N-{4-[2-[(2-thienyl(imino)methyl)-amino]phenyl]ethyl}-benzamide;
3,4,5-trihydroxy-N-{4-[2-[(2-thienyl(imino)methyl)-amino]phenyl]ethyl}-benzamide;
3,4-dihydro-6-hydroxy-2,5,7,8-tetramethyl-N-{4-[(2-thienyl(imino)methyl)amino]phenyl}-2H-1-benzopyran-2-carboxamide;
3,5-bis-(1,1-dimethylethyl)-4-hydroxy-N-{3-[[(2-thienyl(imino)methyl)amino]phenyl]methyl}-benzamide;
N-[3,5-bis-(1,1-dimethylethyl)-4-hydroxyphenyl]-N'-{{4-[(2-thienyl(imino)methyl)amino]phenyl}methyl}-urea;
N-[5-[{3-(3,5-bis-(1,1-dimethylethyl)-4-hydroxyphenyl)-1-oxo-2-propenyl}amino]-2-hydroxyphenyl]-2-thiophenecarboximidamide;
N-[3-[{3-(3,5-bis-(1,1-dimethylethyl)-4-hydroxyphenyl)-1-oxo-2-propenyl}-amino]-4-hydroxyphenyl]-2-thiophenecarboximidamide;
N-[3,5-bis-(1,1-dimethylethyl)-4-hydroxyphenyl]-N'-{{4-[(2-thienyl(imino)methyl)amino]phenyl}carbonylamino}-urea;
N-[3,5-bis-(1,1-dimethylethyl)-4-hydroxyphenyl]-N'-{{4-[(2-thieny(imino)methyl)amino]phenyl}methyl}-thiourea;
N-[3,5-bis-(1,1-dimethylethyl)-4-hydroxyphenyl]-N'-{2-{4-[(2-thienyl(imino)methyl)amino]phenyl}ethyl}-urea;
3,5-bis-(1,1-dimethylethyl)-4-hydroxy-N-{2-[3-[(2-thienyl(imino)methyl)amino]phenyl]ethyl}-benzamide;
2-{4-[(2-thienyl(imino)methyl)amino]phenyl}ethyl 3,5-bis-(1,1-dimethylethyl)-4-hydroxy-benzoate;
2-{3-[(2-thienyl(imino)methyl)amino]phenyl}ethyl 3,5-bis-(1,1-dimethylethyl)-4-hydroxy-benzoate;
2-{2-[(2-thienyl(imino)methyl)amino]phenyl}ethyl 3,5-bis-(1,1-dimethylethyl)-4-hydroxy-benzoate;
and the pharmaceutically acceptable salts thereof.

4. A compound of claim 1 selected from the group consisting of
3,5-bis-(1,1-dimethylethyl)-4-hydroxy-N-[4-[2-thienyl(imino)methyl-amino]phenyl]ethyl]benzamide;
3,4,5-trihydroxy-N-[4-[2-[(2-thienyl(imino)methyl)amino]phenyl]ethyl]-benzamide;
3,4-dihydro-6-hydroxy-2,5,7,8-tetrmethyl-N-[4-[(2-thienyl(imino)methyl)amino]phenyl]-2H-1-benzopyran-2-carboxamide;
3,5-bis-(1,1-dimethylethyl)-4-hydroxy-N-[3-[[(2-thienyl-(imino)methyl)amino]phenyl]methyl]-benzamide;
N-[3,5-bis-(1,1-dimethylethyl)-4-hydroxyphenyl]-N'-[-4-[(2-thienyl(imino)methyl)amino]phenyl]methyl]-urea;
N-[5-[3-(3,5-bis-(1,1-dimethylethyl)-4-hydroxyphenyl)-1-oxo-2-propenyl]-amino[2-hydroxyphenyl]-2-thiophenecarboximidamide;
N-[3-[[3-(3,5-bis-(1,1-dimethylethyl)-4-hydroxyphenyl)-1-oxo-2-propenyl]-amino]-4-hydroxyphenyl]-2-thiophenecarboximidamine; and
N-[3,5-bis-(1,1-dimethylethyl)-4-hydroxyphenyl]-N'-[[4-[(2-thienyl(imino)methyl)amino]phenyl]carbonylamino-urea.

5. A process for the preparation of a compound of claim 1 comprising reacting a compound of the formula

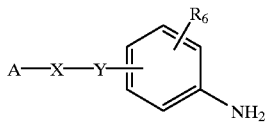

III wherein A, X, Y and $R_6$ are defined as in claim 1 with a compound of the formula

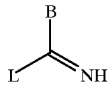

IV wherein B is defined as in claim 1 and L is a leaving group in a lower alkanol to obtain a compound of claim 1.

6. A neuronal NO synthase inhibitory composition comprising a neuronal NO synthase inhibitorily effective amount of claim 1 and an insert pharmaceutical carrier.

7. A inductible NO synthase inhibitory composition comprising a neuronal NO synthase inhibitorily effective amount of claim 1 and an insert pharmaceutical carrier.

8. A method of inhibiting neuronal NO synthase activity in warm-blooded animals comprising administering to warm-blooded animals an neuronal NO synthase inhibitorily effective amount of a compound of claim 1.

9. A method of inhibiting inductible NO synthase activity in warm-blooded animals comprising administering to warm-blooded animals an neuronal NO synthase inhibitorily effective amount of a compound of claim 1.

10. A method of inhibiting lipidic peroxidation in warm-blooded animals comprising administering to warm-blooded animals a lipidic peroxidation inhibitorily effective amount of claim 1.

11. A compound of claim 1 wherein A is

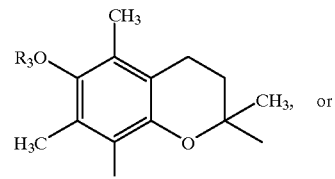

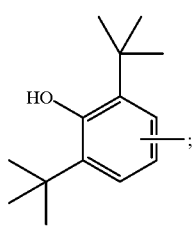

wherein X is —CO— or —NHCO— and Y is selected from the group consisting of —NH—$Z_2$Q and piperazine, Q is selected from the group consisting of a single bond, —$OZ_3$, $NR_3$—$Z_3$ and —$SZ_3$, $Z_2$, and $Z_3$ are individually a single bond or alkylene of 1 to 6 carbon atoms and $R_3$ is hydrogen or alkyl of 1 to 6 carbon atoms.

12. A compound of claim 1 selected from the group consisting of 4-acetoxy-3,5-dimethoxy-N-[4-[2-[2-thienyl-(iminomethyl)-amino]phenyl]ethyl]benzamide; and 3,5-dimethoxy-4-hydroxy-N-[4-[2-[2-thienyl-iminomethyl)-amino]phenyl]ethyl]-benzamide.

* * * * *